United States Patent
Hellerstein

(10) Patent No.: US 7,910,323 B2
(45) Date of Patent: Mar. 22, 2011

(54) METHODS FOR IDENTIFYING THE EFFECT OF A DRUG AGENT ON THE METABOLISM OF SUGARS AND FATS IN AN INDIVIDUAL

(75) Inventor: Marc K. Hellerstein, Kensington, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 12/403,331

(22) Filed: Mar. 12, 2009

(65) Prior Publication Data

US 2010/0041082 A1    Feb. 18, 2010

Related U.S. Application Data

(62) Division of application No. 10/701,990, filed on Nov. 4, 2003, now Pat. No. 7,504,233.

(60) Provisional application No. 60/423,964, filed on Nov. 4, 2002.

(51) Int. Cl.
    *C12Q 1/54* (2006.01)
(52) U.S. Cl. .............................. 435/14; 424/9.1; 424/9.2
(58) Field of Classification Search .................... 435/14; 424/9.1, 9.2
    See application file for complete search history.

(56) References Cited

U.S. PATENT DOCUMENTS

| | | | |
|---|---|---|---|
| 4,065,552 A | 12/1977 | Costa | |
| 4,332,784 A | 6/1982 | Smith et al. | |
| 4,889,126 A | 12/1989 | Doddrell et al. | |
| 4,940,658 A | 7/1990 | Allen et al. | |
| 5,026,909 A | 6/1991 | Zolotarev et al. | |
| 5,042,488 A | 8/1991 | Ackerman | |
| 5,167,948 A | 12/1992 | Wenzel et al. | |
| 5,209,919 A | 5/1993 | Turteltaub et al. | |
| 5,317,098 A | 5/1994 | Shizuya et al. | |
| 5,338,686 A | 8/1994 | Hellerstein | |
| 5,354,662 A | 10/1994 | Stone et al. | |
| 5,376,355 A | 12/1994 | Turteltaub et al. | |
| 5,394,236 A | 2/1995 | Murnick | |
| 5,439,803 A | 8/1995 | Ross et al. | |
| 5,506,147 A | 4/1996 | Kolhouse et al. | |
| 5,597,548 A | 1/1997 | Sherry et al. | |
| 5,665,377 A | 9/1997 | Gonella et al. | |
| 5,665,562 A | 9/1997 | Cook | |
| 5,783,445 A | 7/1998 | Murnick | |
| 5,855,921 A | 1/1999 | Somlyai et al. | |
| 5,910,403 A | 6/1999 | Hellerstein | |
| 5,916,537 A | 6/1999 | Kajiwara et al. | |
| 5,922,554 A | 7/1999 | Fielding et al. | |
| 5,924,995 A | 7/1999 | Klein et al. | |
| 5,961,470 A | 10/1999 | Wagner et al. | |
| 6,010,846 A | 1/2000 | Hellerstein | |
| 6,031,228 A | 2/2000 | Abramson | |
| 6,071,245 A | 6/2000 | Kohno et al. | |
| 6,117,656 A | 9/2000 | Seed | |
| 6,284,219 B1 | 9/2001 | Ajami et al. | |
| 6,329,208 B1 | 12/2001 | Jones et al. | |
| 6,355,416 B1 | 3/2002 | Abramson | |
| 6,461,806 B1 | 10/2002 | Hellerstein | |
| 6,461,870 B2 | 10/2002 | Yatscoff et al. | |
| 6,468,802 B1 | 10/2002 | Yatscoff et al. | |
| 6,599,750 B2 | 7/2003 | Yatscoff et al. | |
| 6,602,715 B2 | 8/2003 | Yatscoff et al. | |
| 6,610,270 B1 | 8/2003 | Ajami | |
| 6,625,547 B1 | 9/2003 | Korzekwa et al. | |
| 6,642,059 B2 | 11/2003 | Chait et al. | |
| 6,653,076 B1 | 11/2003 | Franza, Jr. et al. | |
| 6,653,090 B1 | 11/2003 | Lopaschuk | |
| 6,680,203 B2 | 1/2004 | Dasseux et al. | |
| 6,764,817 B1 | 7/2004 | Schneider | |
| 6,783,751 B2 | 8/2004 | Heumann | |
| 6,808,875 B2 | 10/2004 | Hellerstein | |
| 6,835,927 B2 | 12/2004 | Becker et al. | |
| 6,849,396 B2 | 2/2005 | Schneider | |
| 6,872,575 B2 | 3/2005 | Regnier | |
| 6,887,712 B1 | 5/2005 | Medford et al. | |
| 6,902,719 B2 | 6/2005 | Wagner | |
| 6,906,320 B2 | 6/2005 | Sachs et al. | |
| 7,001,587 B2 | 2/2006 | Hellerstein | |

(Continued)

FOREIGN PATENT DOCUMENTS

| | | |
|---|---|---|
| EP | 0826377 | 3/1998 |
| JP | 2001-211782 A | 8/2001 |
| SU | 968036 | 10/1982 |
| WO | WO-90/11371 | 10/1990 |
| WO | WO-93/20800 | 10/1993 |

(Continued)

OTHER PUBLICATIONS

"NCBI Blast: Protein Sequence (17 letters)," located at <http://blast.ncbi.nlm.nih.gov/Blast.cgi> visited on May 29, 2008, 5 pages.

"New Diagnostic Technique Could Help Treat AIDS," *Agence France-Presse*, Dow Jones News/Retrieval, Feb. 17, 1998, pp. 1-2.

Ackermans, M. T. et al. (2001). "The Quantification of Gluconeogenesis in Healthy Men by 2H2O and [2-13C]Glycerol Yields Different Results: Rates of Gluconeogenesis in Healthy Men Measured with 2H2O are Higher than those Measured with [2-13C]Glycerol," *The Journal of Clinical Endocrinology & Metabolism* 86(5):2220-2226.

(Continued)

*Primary Examiner* — Ralph Gitomer
(74) *Attorney, Agent, or Firm* — Morrison & Foerster LLP

(57) ABSTRACT

Provided herein are methods for determining the metabolism of one or more sugars and/or fatty acids, and applications thereof. Such applications include determining the rate of glycogen synthesis and glycolysis, which are believed to be early markers for predicting elevated risk of diabetes and cardiovascular disease. Other applications include methods for screening drugs that effect sugar and/or fatty acid metabolism. The methods are useful for at least partially characterizing drugs for desirable or undesirable (toxic) characteristics. Drugs that are at least partially characterized using the methods of the invention can then be further developed in pre-clinical testing and clinical trials. Such drugs may be found to be useful in treating obesity, diabetes, cardiovascular disease, and other disorders of metabolism.

19 Claims, 6 Drawing Sheets

U.S. PATENT DOCUMENTS

| | | | |
|---|---|---|---|
| 7,022,834 | B2 | 4/2006 | Hellerstein |
| 7,048,907 | B2 | 5/2006 | Groman et al. |
| 7,057,168 | B2 | 6/2006 | Miller et al. |
| 7,084,396 | B2 | 8/2006 | Schneider |
| 7,255,850 | B2 | 8/2007 | Hellerstein |
| 7,256,047 | B2 | 8/2007 | Malloy et al. |
| 7,262,020 | B2 | 8/2007 | Hellerstein |
| 7,307,059 | B2 | 12/2007 | Hellerstein |
| 7,357,913 | B2 | 4/2008 | Hellerstein |
| 7,410,633 | B2 | 8/2008 | Hellerstein |
| 7,449,171 | B2 | 11/2008 | Hellerstein |
| 7,504,233 | B2 * | 3/2009 | Hellerstein ............ 435/14 |
| 2003/0068634 | A1 | 4/2003 | Hellerstein |
| 2003/0119069 | A1 | 6/2003 | Schneider et al. |
| 2003/0133871 | A1 | 7/2003 | Hellerstein |
| 2003/0148533 | A1 | 8/2003 | Malloy et al. |
| 2003/0180710 | A1 | 9/2003 | Lee et al. |
| 2003/0180800 | A1 | 9/2003 | Lee et al. |
| 2003/0211036 | A1 | 11/2003 | Degani et al. |
| 2003/0224420 | A1 | 12/2003 | Hellerstein et al. |
| 2003/0228259 | A1 | 12/2003 | Hellerstein |
| 2004/0081994 | A1 | 4/2004 | Hellerstein |
| 2004/0115131 | A1 | 6/2004 | Hellerstein |
| 2004/0121305 | A1 | 6/2004 | Wiegand et al. |
| 2004/0152994 | A1 | 8/2004 | Meier-Augenstein |
| 2004/0191916 | A1 | 9/2004 | Gross et al. |
| 2004/0253647 | A1 | 12/2004 | Mathews et al. |
| 2005/0003375 | A1 | 1/2005 | Franza et al. |
| 2005/0014181 | A1 | 1/2005 | Galis et al. |
| 2005/0092910 | A1 | 5/2005 | Geromanos et al. |
| 2005/0118724 | A1 | 6/2005 | Bateman et al. |
| 2005/0153346 | A1 | 7/2005 | Schneider |
| 2005/0175982 | A1 | 8/2005 | Iwatani et al. |
| 2005/0201937 | A1 | 9/2005 | Hellerstein |
| 2005/0202406 | A1 | 9/2005 | Hellerstein |
| 2005/0221278 | A1 | 10/2005 | Iwatani et al. |
| 2005/0238577 | A1 | 10/2005 | Hellerstein |
| 2005/0238581 | A1 | 10/2005 | Kurland et al. |
| 2005/0255509 | A1 | 11/2005 | Hellerstein et al. |
| 2005/0281745 | A1 | 12/2005 | Lee et al. |
| 2006/0008796 | A1 | 1/2006 | Hellerstein |
| 2006/0020440 | A1 | 1/2006 | Hellerstein |
| 2006/0094057 | A1 | 5/2006 | Hellerstein |
| 2006/0100903 | A1 | 5/2006 | Lee et al. |
| 2006/0105322 | A1 | 5/2006 | Iwatani et al. |
| 2006/0105339 | A1 | 5/2006 | Hellerstein |
| 2006/0120961 | A1 | 6/2006 | Schneider et al. |
| 2006/0251576 | A1 | 11/2006 | Hellerstein |
| 2006/0280682 | A1 | 12/2006 | Hellerstein |
| 2007/0248540 | A1 | 10/2007 | Hellerstein |
| 2008/0003179 | A1 | 1/2008 | Hellerstein |
| 2009/0041661 | A1 | 2/2009 | Hellerstein |

FOREIGN PATENT DOCUMENTS

| | | |
|---|---|---|
| WO | WO-93/25705 | 12/1993 |
| WO | WO-95/13096 | 5/1995 |
| WO | WO-98/51820 | 11/1998 |
| WO | 00/12535 A2 | 3/2000 |
| WO | WO-00/13025 | 3/2000 |
| WO | WO-00/63683 | 10/2000 |
| WO | WO-01/80715 | 11/2001 |
| WO | WO-01/84143 | 11/2001 |
| WO | WO-03/061479 | 7/2003 |
| WO | WO-03/068919 | 8/2003 |
| WO | WO-03/087314 | 10/2003 |
| WO | WO-2004/003493 | 1/2004 |
| WO | WO-2004/011426 | 2/2004 |
| WO | WO-2004/021863 | 3/2004 |
| WO | WO-2004/024941 | 3/2004 |
| WO | WO-2004/025270 | 3/2004 |
| WO | WO-2004/042360 | 5/2004 |
| WO | WO-2005/009597 | 2/2005 |
| WO | WO-2005/015155 | 2/2005 |
| WO | WO-2005/033652 | 4/2005 |
| WO | WO-2006/050130 | 5/2006 |
| WO | WO-2006/081521 | 8/2006 |
| WO | WO-2006/107814 | 10/2006 |

OTHER PUBLICATIONS

Adami, H. O. et al. (1995). "The Aetiology and Pathogenesis of Human Breast Cancer," *Mutation Research* 333:29-35.

Airhart, J. et al. (1974). "Compartmentation of Free Amino Acids for Protein Synthesis in Rat Liver," *The Biochemical Journal* 140:539-545.

Ajie, H. O. et al. (1995). "In Vivo Study of the Biosynthesis of Long-Chain Fatty Acids Using Deuterated Water," *The American Journal of Physiology* 269:E247-E252.

Anderson, R.W. et al. (1998). "Direct HIV Cytopathicity Cannot Account for CD4 Decline in AIDS in the Presence of Homeostasis: A Worst-Case Dynamic Analysis," *Journal of Acquired Immune Deficiency Syndromes and Human Retrovirology* 17:245-252.

Antelo, Fernando et al. (2002) "Adipose Triglyceride (TG) Turnover and De Novo Lipogenesis (DNL) in Humans: Measurement by Long-Term 2H2O Labeling and Mass Isotopomer Distribution Analysis (MIDA)" *Experimental Biology* 16 [Meeting Abstract 361.10]:A400.

Asher, E. et al. (1995). "Evaluation of Cell Death in EBV-Transformed Lymphocytes Using Agarose Gel Electrophoresis, Light Microscopy and Electron Microscopy. II. Induction of Non-Classic Apoptosis ("Para-Apoptosis") by Tritiated Thymidine," *Leukemia & Lymphoma* 19:107-119.

Attardi, G. et al. (1988). "Biogenesis of Mitochondria," *Annual Review of Cell Biology* 4:289-333.

Australian Patent Office Search Report mailed Aug. 26, 2005, for Singapore patent application No. SG 200500571-5, filed Jul. 25, 2003, 5 pages.

Austrian Search Report and Written Opinion mailed Aug. 5, 2009, for SG Application No. 200717391-7 filed May 3, 2006, 7 pages.

Bach, S. P. et al. (2000). "Stem Cells: The Intestinal Stem Cell as a Paradigm," *Carcinogenesis* 21(3):469-476.

Bandsma, R. H. et al. (1998). "Contribution of Newly Synthesized Cholesterol to Rat Plasma and Bile Determined by Mass Isotopomer Distribution Analysis: Bile-Salt Flux Promotes Secretion of Newly Synthesized Cholesterol into Bile," *The Biochemical Journal* 329:699-703.

Bandsma, R. H. et al. (2000) "The Contribution of Newly Synthesized Cholesterol to Bile Salt Synthesis in Rats Quantified by Mass Isotopomer Distribution Analysis," *Biochemica et Biophysica Acta* 1483:343-351.

Bertani, R. et al. (2002) "Measurement of Total Body Water (TBW) Through In Vivo Dilution of Tracer Compounds: Use of D2O and its Determination by FT Infrared Spectroscopy," *Annali Di Chimica* 92:135-138.

Bickenbach, J. R. (1981). "Identification and Behavior of Label-Retaining Cells in Oral Mucosa and Skin," *Journal of Dental Research* pp. 1611-1620.

Bier, D. M. (1997). "Stable Isotopes in Biosciences, their Measurement and Models for Amino Acid Metabolism," *European Journal of Pediatrics* 156:S2-S8.

Bier, D. M. (Nov. 1987). "The Use of Stable Isotopes in Metabolic Investigation," *Balliere's Clinical Endocrinology and Metabolism* 1(4):817-836.

Bingham, S.A. (1994). "The Use of 24-h Urine Samples and Energy Expenditure to Validate Dietary Assessments," *The American Journal of Clinical Nutrition* 59(suppl):227S-231S.

Black, G. E. et al. (2001). "Labeling DNA with Stable Isotopes: Economical and Practical Considerations," *BioTechniques* 30:134-138, 140.

Blair, S. N. et al. (1995). "Changes in Physical Fitness and All-Cause Mortality. A Prospective Study of Healthy and Unhealthy Men," *JAMA* 273: 1093-1098.

Blau, K. and Halket, J. eds. (1993) *Handbook of Derivatives for Chromatography*, 2nd Edition, John Wiley & Sons Ltd., England.

Bonotto, S. et al. (1978). "Study of the Distribution and Biological Effects of 3H in the Algae Acetabularia, Chlamydomonas and Porphyra," *Current Topics in Radiation Research Quarterly* 12:115-132.

Boros, L. G. et al. (2001). "Genistein Inhibits Nonoxidative Ribose Synthesis in MIA Pancreatic Adenocarcinoma Cells: A New Mechanism of Controlling Tumor Growth," *Pancreas* 22(1):1-7.

Boros, L. G. et al. (Mar. 2002). "Metabolic Profiling of Cell Growth and Death in Cancer: Applications in Drug Discovery," *Drug Discovery Today* 7(6):364-372.

Bravo, E. et al. (1994). "Decreased Hepatic Uptake and Processing of High Density Lipoprotein Unesterified Cholesterol and Cholesteryl Ester with Age in the Rat," *Journal of Biochemistry* 116:1088-1095.

Brown, A. S. et al. (1998). "Treating Patients with Documented Atherosclerosis to National Cholesterol Education Program-Recommended Low-Density-Lipoprotein Cholesterol Goals with Atorvastatin, Fluvastatin, Lovastatin and Simvastatin," *Journal of the American College of Cardiology* 32:665-672.

Bucy, R.P. et al. (1998) "Analysis of Lymph Node Biopsies in HIV Infected Patients Before and After HAART" Abstract, *5th Conference on Retroviruses and Opportunistic Infections*, Session 66 519:177.

Caldwell, K.A. et al. (1993) "Quantification of Peptide Isotopomer Abundances and Determination of Protein (sic) Turnover Rates by Using Mass Isotopomer Distribution Analysis" Abstract, *41st Annual Amer. Society Mass Spectrometry on Mass Spectrometry*, p. 331a.

Cassella, C.R. et al. (1997) "Mechanisms of Lymphocyte Killing by HIV," *Current Opinion in Hematology* 4:24-31.

Cesar, D. et al. (1998) "Direct Measurement of CD4+ and CD8+ T Cell Proliferation Rates in Vivo in AIDS Patients Using a Stable Isotope-Mass Spectrometric Technique" Abstract, *5th Conference on Retroviruses and Opportunistic Infections*, Chicago Illinois.

Chinkes, D. L. et al. (1996). "Comparison of Mass Isotopomer Dilution Methods Used to Compute VLDL Production In Vivo," *The American Journal of Physiology* 271:E373-E383.

Christiansen, M. P. et al. (Oct. 2000) "Effect of Dietary Energy Restriction on Glucose Production and Substrate Utilization in Type 2 Diabetes," *Diabetes* 49:1691-1699.

Clarke, R. B. (2005). "Isolation and Characterization of Human Mammary Stem Cells," *Cell Proliferation* 38:375-386.

Clayton, D. A. (1991). "Replication and Transcription of Vertebrate Mitochondrial DNA," *Annual Review of Cell Biology* 7:453-478.

Cohen, A. et al. (Oct. 25, 1983) "Purine and Pyrimidine Metabolism in Human T Lymphocytes. Regulation of Deoxyribonucleotide Metabolism," *The Journal of Biological Chemistry* 258(20):12334-12340.

Cohen, J. (1998) "Failure Isn't What It Used to Be . . . But Neither is Success," *Science* 279:1133-1134.

Collins, M. et al. (Mar. 15, 2000) "A Method for Measuring Mitochondrial Proliferation In Vivo Using 2H20 Incorporation Into Mitochondrial DNA," *FASEB Journal* 14(4):A620.

Collins, M. L. et al. (2003). "Measurement of Mitochondrial DNA Synthesis In Vivo Using a Stable Isotope-Mass Spectrometric Technique," *Journal of Applied Physiology* 94:2203-2211.

Connors, M. et al. (1997). "HIV Infection Induces Changes in CD4+ T-Cell Phenotype and Depletions Within the CD4+ T-Cell Repertoire that are Not Immediately Restored by Antiviral or Immune-Based Therapies," *Nature Medicine* 3:533-540.

Conrads, Thomas P. et al. (Jan. 2002). "Stable Isotope Labeling in Proteomics" *The Synthesis Cambridge Isotope Laboratories* 3 (2):1-3.

Craig, S. B. et al. (1996). "The Impact of Physical Activity on Lipids, Lipoproteins, and Blood Pressure in Preadolescent Girls," *Pediatrics* 98:389-395.

Crain, P. F. (1990). "Preparation and Enzymatic Hydrolysis of DNA and RNA for Mass Spectrometry," *Methods in Enzymology* 193:782-790.

Dalvie, D. (2000). "Recent Advances in the Applications of Radioisotopes in Drug Metabolism, Toxicology and Pharmacokinetics," *Current Pharmaceutical Design* 6:1009-1028.

Davis, A. et al. (Jul. 2000). "Effect of Pinitol Treatment on Insulin Action in Subjects with Insulin Resistance," *Diabetes Care* 23(7):1000-1005.

Deeks, S. et al. (1998) "Viral Load and CD4+ T Cell Changes in Patients Failing Potent Protease Inhibitor Therapy" Abstract, *5th Conference on Retroviruses and Opportunistic Infections*, Session 53, 419:158.

Deeks, S. G. et al. (Feb. 1, 2002). "CD4+ T Cell Kinetics and Activation in Human Immunodeficiency Virus-Infected Patients who Remain Viremic Despite Long-Term Treatment with Protease Inhibitor-Based Therapy," *The Journal of Infectious Diseases* 185:315-323.

Dekker, E et al. (1997). "Glucose Homeostasis in Children with Falciparum Malaria: Precursor Supply Limits Gluconeogenesis and Glucose Production" *J Clin Endocrinol Metabol* 82: 2514-2521.

Di Buono, M. et al. (2000). "Comparison of Deuterium Incorporation and Mass Isotopomer Distribution Analysis for Measurement of Human Cholesterol Biosynthesis," *Journal of Lipid Research* 41:1516-1523.

Dimitrov, D.S. et al. (1995) "Scientific Correspondence," *Nature* 375:194-195.

Emken, E. A. (1994). "Metabolism of Dietary Stearic Acid Relative to Other Fatty Acids in Human Subjects," *The American Journal of Clinical Nutrition* 60(Suppl):1023S-1028S.

Emken, Edward A. et al. (1983) "Incorporation of deuterium-labeled trans- and cis-13-octadeconoic acids in human plasma lipids," *Journal of Lipid Research* 24: 34-41.

Etnier, E. L. et al. (1984). "Metabolism of Organically Bound Tritium in Man," *Radiation Research* 100:487-502.

Fagerquist, C. K. et al. (1999). "Molecular Ion Fragmentation and its Effects on Mass Isotopomer Abundances of Fatty Acid Methyl Esters Ionized by Electron Impact," *Journal of the American Society of Mass Spectrometry* 10:430-439.

Fagerquist, C. K. et al. (2001). "Elimination of the Concentration Dependence in Mass Isotopomer Abundance Mass Spectrometry of Methyl Palmitate Using Metastable Atom Bombardment," *Journal of the American Society of Mass Spectrometry* 12:754-761.

Futami, J. et al. (1999). "An Application of the On-line Respiratory Mass Spectrometer to the Detection of *Helicobacter pylori* Infection Using 13C-Labeled Urea," *Journal of the Mass Spectrometry Society of Japan* 47(6):386-388.

Gasparini, P. et al. (Mar. 1989). "Amplification of DNA from Epithelial Cells in Urine," *The New England Journal of Medicine* 320(12):809.

Gerling, B. et al. (1997). "Prediction of Liver Fibrosis According to Serum Collagen VI Level in Children with Cystic Fibrosis," *The New England Journal of Medicine* 336(22):1611-1612.

Gorochov, G. et al. (1998) "Perturbation of CD4+ and CD8+ T-Cell Repertoires During Progression to AIDS and Regulation of the CD4+ Repertoire During Antiviral Therapy," *Nature Medicine* 4:215-221.

Goz, B. (1977). "The Effects of Incorporation of 5-Halogenated Deoxyuridines into the DNA of Eukaryotic Cells," *Pharmacological Reviews* 29:249-272.

Gratzner, H.G. (1982). "Monoclonal Antibody to 5-Bromo- and 5-Iododeoxyuridine: A New Reagent for Detection of DNA Replication," *Science* 218:474-475.

Guo, Z. K. et al. (2000). "De Novo Lipogenesis in Adipose Tissue of Lean and Obese Women: Application of Deuterated Water and Isotope Ratio Mass Spectrometry," *International Journal of Obesity and Related Metabolic Disorders* 24:932-937.

Gygi, Steven et al. (2000) "Using Mass Spectrometry for Quantitative Proteomics" *Proteomics: A Trends Guide*: 31-36.

Hansen, A. P. et al. (1992). "A Practical Method for Uniform Isotopic Labeling of Recombinant Proteins in Mammalian Cells," *Biochemistry* 31:12713-12718.

Heck, S. D. et al. (Apr. 1996). "Posttranslational Amino Acid Epimerization: Enzyme-Catalyzed Isomerization of Amino Acid Residues in Peptide Chains," *Proceedings of the National Academy of Sciences of the United States of America* 93:4036-4039.

Hellerstein, M. et al. (1999) "Directly Measured Kinetics of Circulating T Lymphocytes in Normal and HIV-1-Infected Humans," *Nature Medicine* 5:83-89.

Hellerstein, M. K. (1995). "Methods for Measurement of Fatty Acid and Cholesterol Metabolism," *Current Opinion in Lipidology* 6:172-181.

Hellerstein, M. K. (1996). "Synthesis of Fat in Response to Alterations in Diet: Insights from New Stable Isotope Methodologies," *Lipids* 31(Supp):S117-S125.

Hellerstein, M. K. (1999). "Measurement of T-Cell Kinetics: Recent Methodologic Advances," *Trends Immunology Today* 20(10):438-441.

Hellerstein, M. K. (1999). "The Changing Face of AIDS: Translators Needed," *The American Journal of Clinical Nutrition* 70:787-788.

Hellerstein, M. K. (2001) "No Common Energy: de Novo Lipogenesis as the Road Less Traveled," *The American Journal of Clinical Nutrition* 74:707-708.

Hellerstein, M. K. (2002). "Carbohydrate-Induced Hypertriglyceridemia: Modifying Factors and Implications for Cardiovascular Risk," *Curr Opin Lipidol* 13:33-40.

Hellerstein, M. K. (2004). "New stable isotope-mass spectrometric techniques for measuring fluxes through intact metabolic pathways in mammalian systems: introduction of moving pictures into functional genomics and biochemical phenotyping," *Metabolic Engineering* 6:85-100.

Hellerstein, M. K. et al. (1986). "Glycoconjugates as Noninvasive Probes of Intrahepatic Metabolism: Pathways of Glucose Entry into Compartmentalized Hepatic UDP-glucose Pools during Glycogen Accumulation," *Proceedings of the National Academy of Sciences of the United States of America* 83(18):7044-7048.

Hellerstein, M. K. et al. (1992). "Mass Isotopomer Distribution Analysis: A Technique for Measuring Biosynthesis and Turnover of Polymers," *The American Journal of Physiology* 263:E988-E1001.

Hellerstein, M. K. et al. (1993). "Model for Measuring Absolute Rates of Hepatic de Novo Lipogenesis and Reesterification of Free Fatty Acids," *The American Journal of Physiology* 265:E814-E820.

Hellerstein, M. K. et al. (1994). "Effects of Cigarette Smoking and its Cessation on Lipid Metabolism and Energy Expenditure in Heavy Smokers," *J. Clin. Invest.* 93:265-272.

Hellerstein, M. K. et al. (1997). "Altered Fluxes Responsible For Reduced Hepatic Glucose Production and Gluconeogenesis by Exogenous Glucose in Rats," *The American Journal of Physiology* 272:E163-E172.

Hellerstein, M. K. et al. (1997). "Measurement of Hepatic Ra UDP-glucose in Vivo in Rats: Relation to Glycogen Deposition and Labeling Patterns," *The American Journal of Physiology* 272:E155-E162.

Hellerstein, M. K. et al. (1997). "T Cell Turnover in HIV-1 Disease," *Immunity* 7:583-589.

Hellerstein, M. K. et al. (1999). "Mass Isotopomer Distribution Analysis at Eight Years: Theoretical, Analytic, and Experimental Considerations," *The American Journal of Physiology* 276:E1146-E1170.

Hellerstein, M. K. et al. (2002) "Measurement of Synthesis Rates of Slow-turnover Proteins from 2H2O Incorporation into Non-essential Amino Acids (NEAA) and Application of Mass Isotopomer Distribution Analysis (MIDA)," *FASEB Journal Experimental Biology 2002: Meeting Abstracts* 16:A256.

Hellerstein, M. K. et al. (Sep. 1997). "Hepatic Gluconeogenic Fluxes and Glycogen Turnover During Fasting in Humans. A Stable Isotope Study," *The Journal of Clinical Investigation* 100(5):1305-1319.

Hellerstein, M.K. et al. (1994) "Mass Isotopomer Distribution Analysis for Measuring Fluxes Through Intracellular Metabolic Pathways and Biosynthetic Rates of Polymers" *IFAC Modeling and Control in Biomedical Systems*, pp. 353-359.

Hellerstein, Marc K. (2003) "In Vivo Measurement of Fluxes Through Metabolic Pathways: The Missing Link in Functional Genomics and Pharaceutical Research," *Annu. Rev. Nutr.* 23:379-402.

Ho, D. D. et al. (1995). "Rapid Turnover of Plasma Virions and CD4 Lymphocytes in HIV-1 Infection," *Nature* 373:123-126.

Hoh, R. et al. (1998). "De Novo Lipogenesis Predicts Short-Term Body-Composition Response by Bioelectrical Impedance Analysis to Oral Nutritional Supplements in HIV-Associated Wasting," *The American Journal of Physiology* 68:154-163.

Hsieh, E. A. et al. (2004). "Dynamics of Keratinocytes in Vivo Using 2H2O Labeling: A Sensitive Marker of Epidermal Proliferation State," *J Invest Dermatol* 123:530-536.

Hudgins, L. C. et al. (1996). "Human Fatty Acid Synthesis is Stimulated by a Eucaloric Low Fat, High Carbohydrate Diet," *J. Clin. Invest.* 97(9):2081-2091.

Hudgins, L. C. et al. (2000). "Relationship Between Carbohydrate-Induced Hypertriglyceridemia and Fatty Synthesis in Lean and Obese Subjects," *J. Lipid Res.* 41:595-604.

Hulzebos, C. V. et al. (2001). "Measurement of Parameters of Cholic Acid Kinetics in Plasma using a Microscale Stable Isotope Dilution Technique: Application to Rodents and Humans," *Journal of Lipid Research* 42:1923-1929.

Humphrey, T. J. et al. (1975). "A New Method for the Measurement of Protein Turnover," *Biochem. J.* 148:119-127.

Humphrey, T. J. et al. (1976) "A Sensitive Method for Measuring Protein Turnover Based on the Measurement of 2-3H-labeled Amino Acids in Proteins," *Biochem. J.* 156:561-568.

International Search Report and Written Opinion mailed Aug. 8, 2006, for international application No. PCT/US05/10429, filed Mar. 29, 2005, 16 pages.

International Search Report and Written Opinion mailed Feb. 5, 2008, for PCT Application No. PCT/US2006/017167 filed May 3, 2006, 11 pages.

International Search Report and Written Opinion mailed Oct. 11, 2007, for PCT Application No. PCT/US05/05660 filed 22, 2005, 11 pages.

International Search Report mailed Aug. 1, 2005, for PCT application No. PCT/US2005/08265, filed Mar. 11, 2005, 4 pages.

International Search Report mailed Aug. 18, 2004, for PCT application PCT/US03/23340, filed Jul. 25, 2003, 3 pages.

International Search Report mailed Jul. 8, 2004, for PCT patent application No. PCT/US03/27623 filed on Sep. 4, 2003, 3 pages.

International Search Report mailed on Apr. 13, 2004, for PCT application No. PCT/US03/20052 filed on Jun. 25, 2003, 2 pages.

International Search Report mailed on Apr. 4, 2005, for PCT application No. PCT/US04/21063 filed on Jun. 29, 2004, 2 pages.

International Search Report mailed on Aug. 18, 2004, for PCT application PCT/US03/29526, filed Sep. 16, 2003, 1 page.

International Search Report mailed on Aug. 20, 2004, for PCT application No. PCT/US03/10554 filed on Apr. 4, 2003, 4 pages.

International Search Report mailed on Jan. 19, 2005, for PCT application No. PCT/US03/29361 filed on Sep. 15, 2003, 3 pages.

International Search Report mailed on Jul. 9, 2004, for PCT application No. PCT/US03/35107 filed on Nov. 4, 2003, 2 pages.

International Search Report mailed on Jun. 29, 2004, for PCT application No. PCT/US03/04183 filed on Feb. 12, 2003, 4 pages.

International Search Report mailed on Mar. 25, 2005, for PCT application No. PCT/US04/39722 filed on Nov. 24, 2004, 2 pages.

Iyengar, V. et al. (1991). "Human Stools as a Source of Viable Colonic Epithelial Cells," *The FASEB Journal* 5:2856-2859.

James, J.S. (1998) "Clinical Implications of Virological Failure: Interview with Steven Deeks, M.D., San Francisco General Hospital," *AIDS Treatment News*, 289:6-7.

Jennings, G. et al. (Jul. 1999) "The Use of Infrared Spectrophotometry for Measuring Body Water Spaces," *Clinical Chemistry* 45(7): 1077-1081.

Jones, J. G. (2001). "An Integrated 2H and 13C NMR Study of Gluconeogenesis and TCA Cycle Flux in Humans," *American Journal of Physiology-Endocrinology and Metabolism* 281:E848-856.

Jones, P. J. J. et al. (1990). "Evidence for Diurnal Periodicity in Human Cholesterol Synthesis," *Journal of Lipid Research* 31:667-673.

Jones, Peter J.H. et al. (1994). "Interaction of Dietary Fat Saturation and Cholesterol Level on Cholesterol Synthesis Measured Using Deuterium Incorporation," *Journal of Lipid Research* 35: 1093-1101.

Jung, Hye Rim. et al. (1999) "Metabolic Adaptations to Dietary Fat Malabsorption in Chylomicron-Deficient Mice," *Biochem. J.* 343: 473-478.

Jungas, Robert L. (1968) "Fatty Acid Synthesis in Adipose Tissue Incubated in Tritiated Water," *Biochemistry* 7(10): 3708-3717.

Katz, J. et al. (1976). "Futile Cycles in the Metabolism of Glucose," *Curr Top Cell Regul* 10: 237-89.

Kelleher, Joanne K. et al. (1992) "Model Equations for Condensation Biosynthesis Using Stable Isotopes and Radioisotopes," *Am. J. Physiol.* 262: E118-E125.

Khairallah, E. A. et al. (1976). "Assessment of Protein Turnover in Perfused Rat Liver: Evidence for Amino Acid Compartmentation from Differential Labeling of Free and tRNA-bound Valine," *J Biol Chem* 251(5): 1375-1384.

Kim, J. et al. (2000) "A New Stable Isotope-Mass Spectrometric (MS) Method to Measure Proliferation Rates of Colon Epithelial Cells," *FASEB Journal* 14(4): A718.

Lammert, Ole et al. (2000) "Effects of Isoenergetic Overfeeding of Either Carbohydrate or Fat in Young Men," *British Journal of Nutrition* 84:233-245.

Lee, Chong Do et al. (1999) "Cardiorespiratory Fitness, Body Composition, and All-Cause and Cardiovascular Disease Mortality in Men 1-3," *Am J Clin Nutr* 69:373-380.

Lefebvre, P. J. (Jan. 1979). "Naturally Labeled 13C-Glucose: A New Tool to Measure Oxidation Rates of Exogenous Glucose," *Diabetes* 28(Suppl. 1): 63-65.

Leung, Gordon K. et al. (2000) "A Deficiency of Microsomal Triglyceride Transfer Protein Reduces Apolipoprotein B Secretion," *The Journal of Biological Chemistry* 275(11):7515-7520.

Lewanczuk, Richard Z. et al. (2004) "Comparison of the [13 C] Glucose Breath Test to the Hyperinsulinemic-Euglycemic Clamp When Determining Insulin Resistance," *Diabetes Care* 27(2):441-447.

Lipkin, M. (1987) "Proliferation and Differentiation of Normal and Diseased Gastrointestinal Cells," *In Physiology of the Gastrointestinal Tract*, L.R. Johnson ed., Raven Press, New York, pp. 255-284.

Lipkin, M. et al. (1963). "Cell Proliferation Kinetics in the Gastrointestinal Tract of Man. I. Cell Renewal in Colon and Rectum," *Journal of Clinical Investigations* 42(6):767-776.

Lutton, C. et al. (1990) "Critical analysis of the Use of 14C-acetate for Measuring In Vivo Rat Cholesterol Synthesis," *Reprod Nutr Dev* 30: 71-84.

MacAllan, Derek C. et al. (1998) "Measurement of Cell Proliferation by Labeling of DNA with Stable Isotope-Labeled Glucose: Studies in Vitro, in Animals, and in Humans," *Proc. Natl. Acad. Sci.* 95: 708-713.

Maentausta, O. et al. (1979). "Radioimmunoassay of Conjugated Cholic Acid, Chenodeoxycholic Acid, and Deoxycholic Acid from Human Serum, with Use of 125I-Labeled Ligands," *Clin. Chem.* 25(2): 264-268.

Margolick, J.B. et al. (1995) "Failure of T-cell Homeostasis Preceding AIDS in HIV-1 Infection," *Nature Medicine* 1(7):674-680.

Maric, D. et al. (2000). "Functional Ionotropic Glutamate Receptors Emerge During Terminal Cell Division and Early Neuronal Differentiation of Rat Neuroepithelial Cells," *Journal of Neuroscience Research* 61(6):652-662.

Marin, S. et al. (2004). "Dynamic Profiling of the Glucose Metabolic Network in Fasted Rat Hepatocytes using [1,2-13C2]Glucose," *Biochemical Journal* 381:287-294.

Martin et al. (1998). "Discovery of a human liver glycogen phosphorylase inhibitor that lowers blood glucose in vivo," *Proc. Natl. Acad. Sci. USA* 95(4):1776-1781.

Mathur-De Vré, R. et al. (1984) "Molecular Aspects of Tritiated Water and Natural Water in Radiation Biology," *Prog. Biophys. Molec. Biol.* 43: 161-193.

McCloskey, J.A. (1990) "ElectronIonization Mass Spectra of Trimethylsilyl Derivatives of Nucleosides," *Meth. Enz.* 193:825-841.

McCune, J.M. (1997). "Thymic Function in HIV-1 Disease," *Seminars in Immunology* 9:397-404.

McCune, Joseph M. et al. (2000) "Factors Influencing T-Cell Turnover in HIV-1-Seropositive Patients," *J. Clin. Invest.* 105:R1-R8.

McLean, A.R. et al. (1995) "In Vivo Estimates of Division and Death Rates of Human T Lymphocytes," *Proc. Natl. Acad. Sci USA* 92:3707-3711.

Meier, P.R. et al. (Mar. 1981) "Rates of Protein Synthesis and Turnover in Fetal Life," *Am J Physiol.* 240(3):E320-E324.

Mellors, J.W. et al. (1995) "Quantitation of HIV-1 RNA in Plasma Predicts Outcome after Seroconversion," *Ann. Intern. Med.* 122:573-579.

Mellors, J.W. et al. (1996) "Prognosis in HIV-1 Infection Predicted by the Quantity of Virus in Plasma," *Science* 272:1167-70.

Messmer, Bradley T. et al. (Feb. 10, 2005) "In Vivo Measurements Document the Dynamic Cellular Kinetics of Chronic Lymphocytic Leukemia B Cells," *J. Clin. Invest.* doi:10.1172/JCI200523409.

Mewissen, D.J. et al. (1977). "Comparative Incorporation of Tritium from Tritiated Water Versus Tritiated Thymidine, Uridine or Leucine," *Curr Top Rad Res Quart* 12: 225-254.

Michie, C.A. et al. (1992) "Lifespan of Human Lymphocyte Subsets Defined by CD45 Isoforms," *Nature* 360:264-265.

Mikkola, T. S. et al. (2003). "Serum Cholesterol Efflux Potential is an Independent Predictor of Coronary Artery Atherosclerosis," *Atherosclerosis* 170:31-38.

Mindham, M. A. et al. (1994). "Application of Simultaneous Spleen and Liver Perfusion to the Study of Reverse Cholesterol Transport," *Biochemical Journal* 302:207:213.

Misell, L. et al. (2000) "A new in Vivo Stable Isotope Method for Measuring Mammary Epithelial Cell Proliferation," *FASEB Journal Experimental Biology* 2000 14(4), Meeting Abstract 550.5: A786.

Mohri, Hiroshi et al. (2001) "Increased Turnover of T Lymphocytes in HIV-1 Infection and its Reduction by Antiretroviral Therapy," *J. Exp. Med.* 194(9): 1277-1287.

Morris, Rebecca J. et al. (1997). "Evidence that a Slowly Cyling Subpopulation of Adult Murine Epidermal Cells Retains Carcinogen," *Cancer Research* 46: 3061-3066.

Morris, Rebecca J. et al. (1997). "Evidence that Cutaneous Carcinogen-initiated Epithelial Cells from Mice are Quiescent Rather than Actively Cyling," *Cancer Research* 57:3436-3443.

Morsches, Bernhard (1976). "Tierexperimentelle Untersuchungen uber die Beziehungen zwischen der Hydroxyprolinausscheidung im Urin und den Hydroxyprolinfraktionen im Serum," *Der Hautarzt* 27: 234-242.

Mosier, D.E. (1995) "CD4.sup.+ Cell Turnover," *Nature* 375:193-194.

Murali-Krishna, K. et al. (1998) "Counting Antigen-Specific CD8 T Cells: A Reevaluation of Bystander Activation during Viral Infection," *Immunity* 8:177-187.

Nagasaka, S. et al. (May 1999). "Endogenous Glucose Production and Glucose Effectiveness in Type 2 Diabetic Subjects Derived From Stable-Labeled Minimal Modal Approach," *Diabetes* 48:1054-1056.

Naik, S. U. et al. (2006). "Pharmacological Activation of Liver X Receptors Promotes Reverse Cholesterol Transport In Vivo," *Circulation* 113:90-97.

Nanjee, M. N. et al. (2001). "Intravenous apoA-I/lecithin Discs Increase Pre-Beta-HDL Concentration in Tissue Fluid and Stimulate Reverse Cholesterol Transport in Humans," *Journal of Lipid Research* 42:1586-1593.

Neese, R. A. et al. (1993) "Measurement of Endogenous Synthesis of Plasma Cholesterol in Rats and Humans Using MIDA," *Am. J. Physiol.* 264: E139-E147.

Neese, R. A. et al. (Nov. 2002) "Measurement in Vivo of Proliferation Rates of Slow Turnover Cells by 2H2O Labeling of the Deoxyribose Moiety of DNA," *PNAS* 99(24): 15345-15350.

Neese, Richard A. et al. (1995) "Gluconeogenesis and Intrahepatic Triose Phosphate Flux in Response to Fasting or Substrate Loads," *Journal of Biological Chemistry* 270(24): 14452-14463.

Neese, Richard A. et al. (2001) "Advances in the Stable Isotope-Mass Spectrometric Measurement of DNA Synthesis and Cell Proliferation," *Analytical Biochemistry* 298(2): 189-195.

Ong, Shao-En et al. (2002) "Stable Isotope Labeling by Amino Acids in Cell Culture, SILAC, as a Simple and Accurate Approach to Expression Proteomics," *Molecular and Cellular Proteomics* 1: 376-386.

Oshima, M. et al. (2002). "COX Selectivity and Animal Models for Colon Cancer," *Current Pharmaceutical Design* 8:1021-1034.

Ouguerram, K. et al. (Jan. 2002) "A New Labeling Approach Using Stable Isotopes to Study In Vivo Plasma Cholesterol Metabolism in Humans," *Metabolism* 51(1): 5-11.

Oyaizu, N. et al. (1995) "Role of Apoptosis in HIV Disease Pathogenesis," *J. of Clinical Immunology* 15(5):217-231.

Paku, S. (Apr. 2001). "Origin and Structural Evolution of the Early Proliferating Oval Cells in Rat Liver," *American Journal of Pathology* 158(4):1313-1323.

Palmer, L.D. et al. (1997). "Telomere Length, Telomerase Activity, and Replicative Potential in HIV Infection: Analysis of CD4+ and CD8+ T Cells from HIV-discordant Monozygotic Twins," *J. Experimental Medicine* 185(7):1381-1386.

Panteleo, Giuseppe (1999) "Unraveling the Strands of HIV's Web," *Nature Medicine* 5(1): 27-28.

Papageorgopoulos, C. et al.(1993) "Toward the Measurement of Protein Synthesis by Mass Isotopomer Distribution Analysis (MIDA):Resolution of Isotopomers in a [d.sub.3 ]-Leucine Enriched Synthetic Oligopeptide Using Electrospray/Quadrupole Mass Spectrometry (ESI/MS)," Abstract, *Federation of American Societies for Experimental Biology* 1022:A177.

Papageorgopoulos, Christina et al. (1999) "Measuring Protein Synthesis by Mass Isotopomer Distribution Analysis (MIDA)," *Analytical Biochemistry* 267: 1-16.

Park, S. S., et al. (1997). "Measurement of Small Intestinal Cell Turnover with [6,6, 2H2] Glucose," *Berkeley Scientific*, Abstract 1(2):41-43.

Parks, Elizabeth J. et al. (1999) "Effects of a Low-Fat, High-Carbohydrate Diet on VLDL-Triglyceride Assembly, Production, and Clearance," *J. Clin. Invest.* 104(8): 1087-1096.

Parks, Elizabeth J. et al. (2000) "Carbohydrate-induced Hypertriacylglycerolemia: Historical Perspective and Review of Biological Mechanisms," *Am. J. Nutr.* 71: 412-433.

Parks, Elizabeth J. et al. (2000) "Dependence of Plasma a-Tocopherol Flux on Very Low-Density Triglyceride Clearance in Humans," *Free Radical Biology & Medicine* 29(11): 1151-1159.

Paša-Tolic, Ljiljana et al. (1999) "High Throughput Proteome-Wide Precision Measurements of Protein expression Using Mass Spectrometry," *J. Am. Chem. Soc.* 121: 7949-7950.

Patsalos, P. N. et al. (Oct. 1980). "Pattern of Myelin Breakdown During Sciatic Nerve Wallerian Degeneration: Reversal of the Order of Assembly," *The Journal of Cell Biology* 87:1-5.

Patterson, Bruce W. et al. (1993) "Concentration Dependence of Methyl-Palmitate Isotope Ratios by Electron Impact Ionization Gas Chromatography/Mass Spectrometry," *Biol. Mass Spectrom.* 22: 481-486.

Patterson, Bruce W. et al. (Aug. 1997). "Measurement of Very Low Stable Isotope Enrichments by Gas Chromatography/Mass Spectrometry: Application to Measurement of Muscle Protein Synthesis," *Metabolism* 46(8): 943-948.

Patton, G.M. et al. (Jul. 1979). "Measurements of Fatty Acid Synthesis by Incorporation of Deuterium from Deuterated Water," *Biochemistry* 18(14):3186-3188.

Perelson, A.S. et al.(1996) "HIV-1 Dynamics in Vivo: Virion Clearance Rate, Infected Cell Life-Span, and Viral Generation Time," *Science* 271:1582-1586.

Perelson, A.S. et al.(1997). "Decay Characteristics of HIV-1-Infected Compartments During Combination Therapy," *Nature* 387:188-191.

Perochon, E. et al. (1997). "Radiolabeling of the Lipids of Chinese Hamster Ovary Cells with the Probe [3-(Trifluoromethyl)-3-(m-[125]iodophenyl)diazirine]," *Analytical Biochemistry* 254:109-118.

Pozharisski, K.M. et al. (1980) "Study of Kinetics of Epithelial Cell Populations in Normal Tissues of the Rat's Intestines and in Carcinogenesis," *Exp. Path.*, Bd. 18:387-406.

Previs, Stephen F. et al. (2001) "Estimation of Protein Turnover In Vivo Using D2O" *Diabetes Abstract Book*, 61st Scientific Sessions 50[Supplement 2]: A301.

Propper, D. J. et al. (Jan. 2003). "Use of Positron Emission Tomography in Pharmacokinetic Studies to Investigate Therapeutic Advantage in a Phase I Study of 120-Hour Intravenous Infusion XR5000," *Journal of Clinical Oncology* 21(2):203-210.

Ravichandran, L.V. et al., (Jun. 1991) "In vivo labeling studies on the biosynthesis and degradation of collagen in experimental myocardial infarction," *Biochemistry Journal* 24(3): 405-414.

Reichard, P. (1978). "From Deoxynucleotides to DNA Synthesis," *Federation Proceedings* 37(1):9-14.

Reichard, P. (1988) "Interactions Between Deoxyribonucleotide and DNA Synthesis," *Ann. Rev. Biochem.* 57:349-374.

Rittenberg, D. et al. (Feb. 1937). "Deuterium as an Indicator in the Study of Intermediary Metabolism-VIII. Hydrogenation of Fatty Acids in the Animal Organism," *Journal of Biological Chemistry* 117:485-490.

Rittenberg, D. et al. (Sep. 1937). "Deuterium as an Indicator in the Study of Intermediary Metabolism-X. The Metabolism of Butyric and Caproic Acids," *Journal of Biological Chemistry* 120:503-510.

Rittler, P. et al. (2003). "Effect of Tumor Removal on Mucosal Protein Synthesis in Patients with Colorectal Cancer," *American Journal of Physiology-Endocrinology and Metabolism* 284:E1018-E1021.

Roberts, S.B. (1989) "Use of the Doubly Labeled Water Method for Measurement of Energy Expenditure, Total Body Water, Water Intake, and Metabolizable Energy Intake in Humans and Small Animals," *Can. J. Physiol. Pharmacol.* 67(10): 1190-1198.

Robin, Eugene D. et al. (1988). "Mitochondria DNA Molecules and Virtual Number of Mitochondria per Cell in Mammalian Cells," *Journal of Cellular Physiology* 136:507-513.

Robosky, L. C. (2002). "In Vivo Toxicity Screening Programs Using Metabonomics," *Combinatorial Chemistry & High Throughput Screening* 5:651-662.

Rocha, B. et al. (1990) "Accumulation of Bromodeoxyuridine-Labelled Cells in Central and Peripheral Lymphoid Organs: Minimal Estimates of Production and Turnover Rates of Mature Lymphocytes," *Eur. J. Immunol.* 20:1697-1708.

Roda, Aldo et al. (1980). "Results with Six 'Kit' Radioimmunoassays for Primary Bile Acids in Human Serum Intercompared," *Clin. Chem.* 26(12): 1677-1682.

Roederer, M. (Jul. 1995) "T-Cell Dynamics of Immunodeficiency," *Nature Medicine* 1(7):621-622.

Rooyackers, Olav E. et al. (Oct. 1996) "Tracer Kinetics Are of Limited Value to Measure In Vivo Protein Synthesis and Degradation Rates in Muscle of Anesthetized Rats," *Metabolism* 45(10): 1279-1283.

Rosin, M. P. et al. (Dec. 1, 1997). "The Use of Exfoliative Cell Samples to Map Clonal Genetic Alterations in the Oral Epithelium of High-Risk Patients," *Cancer Research* 57:5258-5260.

Royale, G. T. et al. (1981). "Techniques for Investigating Substrate Metabolism in Patients," *Annals of the Royal College of Surgeons of England* 63:415-419.

Sakurai, Y. (1996). "The Meanings of Measuring Biological Metabolism Using a Stable Isotope Labeled Tracer: The Difference in Metabolism Between a Healthy Human and a Patient in Surgically Serious Condition," *Medical Journal of Fukita Academy* 20(1):9-21.

Sawada, S. et al. (1995) "Comparison of Autoradiography, Liquid Scintillation Counting and Immunoenzymatic Staining of 5-bromo-2'-deoxyuridine for Measurement of Unscheduled DNA Synthesis and Replicative DNA Synthesis in Rat Liver," *Mutation Research* 344:109-116.

Scalise, K. (Feb. 11-17, 1998) "Tracking T-Cells in AIDS Patients: A Safe Reliable Method of Measuring Human Cell Generation Rates," *Berkeleyan* p. 3.

Scheibner, J et al. (1993) "Bile Acid Synthesis from Newly Synthesized Vs. Preformed Cholesterol Precursor Pools in the Rat," *Hepatology* 17: 1095-1102.

Scheibner, J et al. (1999) "Complex Feedback Regulation of Bile Acid Synthesis in the Hamster: The Role of Newly Synthsized Cholesterol," *Hepatology* 30: 230-237.

Schneiter, P. et al. (1998). "Kinetics of Dexamethasone Induced Alterations of Glucose Metabolism in Healthy Humans," *American Journal of Physiology* pp. E806-E813.

Schoenheimer, R. et al. (1935). "Deuterium as an Indicator in the Study of Intermediary Metabolism-III. The Role of the Fat Tissues," The Journal of Biological Chemistry 111:175-181.

Schoenheimer, R. et al. (Mar. 1936). "Deuterium as an Indicator in the Study of Intermediary Metabolism-V. The Desaturation of Fatty Acids in Organism," *Journal of Biological Chemistry* 113:505-510.

Schoenheimer, R. et al. (1937). "Deuterium as an Indicator in the Study of Intermediary Metabolism-IX. The Conversion of Stearic Acid into Palmitic Acid in the Organism," The Journal of Biological Chemistry 120:155-165.

Schwarz, Jean-Marc et al. (1995) "Short-Term Alterations in Carbohydrate Energy Intake in Humans," *J. Clin. Invest.* 96: 2735-2743.

Shevchenko, Andrej et al. (1997) "Rapid 'de Novo' Peptide Sequencing by a Combination of Nanoelectrospray, Isotopic Labeling and a Quadrupole/Time-of-flight Mass Spectrometer," *Rapid Commun. Mass Spectrom.* 11: 1015-1024.

Shigenaga, M.K. et al. (1994) "Assays of Oxidative DNA Damage Biomarkers 8-Oxo-2'-deoxyguanosine and 8-Oxoguanine in Nuclear DNA and Biological Fluids by High-Performance Liquid Chromatography with Electrochemical Detection," *Methods in Enzymology* 234:16-33.

Siler, Scott Q. et al. (1998) "The Inhibition of Gluconeogenesis Following Alcohol in Humans," *Am. J. Physiol.* 275: E897-E907.

Siler, Scott Q. et al. (1998) "VLDL-Triglyceride Production After Alcohol Ingestion, Studied Using [2-13C1] Glycerol," *J. Lipid Res.* 39: 2319-2328.

Smith, et al. (1983) "The Phosphogluconate Odixative Pathway," in *Principles of Biochemistry*, 7th edition, McGraw-Hill Book Company, pp. 417-423.

Sosa-Peinado, A. et al. (Jul. 2000). "Overexpression and Biosynthetic Deuterium Enrichment of TEM-1 Beta-Lactamase for Structural Characterization by Magnetic Resonance Methods," *Protein Expression and Purification* 19(2):235-245.

Sprent, J. et al. (1995) "CD4+ Cell Turnover," *Nature* 375:194.

Stingl et al. (2001). *Breast Can Res and Treatment*, 67:93-109.

Stingl et al. (Feb. 2006). *Nature* 439:993-997.

Sunter, J.P. et al. (1978). "Cell Population Kinetics in the Epithelium of the Colon of the Male Rat." *Virchows Archiv. B Cell Path.* 26: 275-287.

Supplementary European Search Report mailed Jul. 28, 2009, for EP Application No. 04809469.2 filed Jun. 29, 2004, 4 pages.

Supplementary European Search Report mailed Jun. 30, 2009, for EP Application No. 05725448.4 filed Mar. 11, 2005, 7 pages.

Supplementary European Search Report mailed Sep. 19, 2008, for EP Application No. 05733311.4 filed Feb. 2, 2005, 9 pages.

Supplementary Partial European Search Report mailed Aug. 17, 2005, for EP Application No. 03749756.7 filed Sep. 15, 2003, 6 pages.

Supplementary Partial European Search Report mailed Jul. 25, 2006, for EP Application No. 02806603.3 filed Oct. 23, 2002, 5 pages.

Supplementary Partial European Search Report mailed Mar. 9, 2006, for European Patent Application No. EP 03713429.3, filed Feb. 12, 2003, 6 pages.

Supplementary Partial European Search Report mailed Sep. 22, 2006, for European patent application No. EP 03768624.3, filed Nov. 4, 2003, 4 pages.

Teixeira, L et al. (2001) "Poor CD4 T Cell Restoration After Supression of HIV-1 Replication May Reflect Lower Thymic Function," *AIDS* 15(14):1749-1756.

Tint, G.S. et al. (1974). "Transformation of 5α-cholest-7-en-3β-ol to Cholestanol and Cholestanol in Cerebrotendinous Xanthomatosis," *Journal of Lipid Research* 15: 256-262.

Traber, P.G. et al. (1991) "Isolation of Intestinal Epithelial Cells for the Study of Differential Gene Expression Along the Crypt-Villus Axis," *Am. J. Physiol.* 260:G895-G903.

Trappe, T. A. et al. (2002) "Effect of Ibuprofen and Acetaminophen on Postexercise Muscle Protein Synthesis," *Am J Physiol Endocronol Metab* 282: E551-E556.

Turner, S. M. (2006). "Stable Isotopes, Mass Spectrometry, and Molecular Fluxes: Applications to Toxicology," *Journal of Pharmacological and Toxicological Methods* 53:75-85.

Turner, S. M. et al. (2005). "Emerging Applications of Kinetic Biomarkers in Preclinical and Clinical Drug Development," *Current Opinion in Drug Discovery & Development* 8(1): 115-126.

Turner, Scott M. et al. (2002) "Measurement of Triglyceride (TG) Synthesis in Vivo 2H2O Incorporation into TG-Glycerol and Application of Mass Isotopomer Distribution Analysis (MIDA)," *Experimental Biology* 2002 16[Meeting Abstract 361.9]: A400.

U.S. Office Action mailed on Dec. 14, 2007, for U.S. Appl. No. 10/701,990, filed Nov. 4, 2003, 8 pages.

U.S. Office Action mailed on Jan. 24, 2007, for U.S. Appl. No. 10/701,990, filed Nov. 4, 2003, 6 pages.

Van Hinsbergh, V.W.M. et al. (1978). "Palmitate Oxidation by Rat Skeletal Muscle Mitochondria," *Archives of Biochemistry and Biophysics* 190(2): 762-771.

Van Loan, Marta D. et al. (1999) "Monitoring Changes in Fat-Free Mass in HIV-Positive Men With Hypotestosteronemia and AIDS Wasting Syndrome Treated With Gonadal Hormone Replacement Therapy," *AIDS* 13:241-248.

Veenstra, Timothy D. et al. (2000) "Proteome Analysis Using Selective Incorporation of Isotopically Labeled Amino Acids," *J. Am. Soc. Mass. Spectrom.* 11: 78-82.

Veerkamp, Jacques H. et al. (1986) "14CO2 Production Is No Adequate Measure of [14C]Fatty Acid Oxidation," *Biochemical Medicine and Metabolic Biology* 35: 248-259.

Véniant, Murielle M. et al. (2000) "Defining the Atherogenicity of Large and Small Lipoproteins Containing Apolipoproteins B100," *J. Clin. Invest.* 106(12): 1501-1510.

Wadke, M. et al. (Jul. 1973). "Fatty Acid Synthesis by Liver Perfused with Deuterated and Tritiated Water," *Biochemist* 12(14):2619-2624.

Wain-Hobson, S. (1995) "Virological Mayhem," *Nature* 373:102.

Waldeman, F.M. et al. (1991) "A Comparison Between Bromodeoxyuridine and 3 H Thymidine Labeling in Human Breast Tumors," *Modern Path.* 4(6):718-722.

Wang, Wei et al. (2000) "Effects of Nicotinic Acid on Fatty Acid Kinetics, Fuel Selection, and Pathways of Glucose Production in Women," *Am. J. Physiol. Endocrinol. Metab.* 279: E50-E59.

Waterlow, J.C. (1980) "Protein Turnover in the Whole Animal," *Invest. Cell Pathol.* 3: 107-119.

Wei, X et al. (1995) "Viral Dynamics in Human Immunodeficiency Virus Type 1 Infection," *Nature* 373:117-122.

Winett, Richard et al. (2000) "Exercise Regimens for Men With HIV," *JAMA* 284(2): 175-6.

Wolf, George (1995) "The Effect of Fasting and Fructose and Glucose Infusion on Gluconeogenesis and Triose Phosphate Flux in Rats in Vivo," *Nutrition Reviews* 53(10): 299-302.

Wolfe, R. (1990) "Isotopic Measurement of Glucose and Lactate Kinetics," *Ann. Med.* 22:163-170.

Wolfe, R. et al. (1984). "Glucose Metabolism in Humans," *ACS Symposium Series* 258, Chapter 12, Turnund et al. ed., pp. 175-189.

Wolthers et al. (1998) "Rapid CD4+ T-Cell Turnover in HIV-1 Infection: a Paradigm Revisited," *Immunol. Today* 19(1):44-48.

Wolthers, K. C. et al. (1996) "T Cell Telomere Length in HIV-1 Infection: No Evidence for Increased CD4+ T Cell Turnover," *Science* 274:1543-1547.

Wood, H. G. et al. (1963) "Estimation of Pathways of Carbohydrate Metabolism," *Biochemische Zeitschrift* 338:809-847.

Written Opinion mailed Jul. 14, 2006, by the Australian Patent Office for Singapore patent application No. 200502593-7, filed Nov. 4, 2003, 5 pages.

Zhang, B.-L. et al. (2006). "Deuterium NMR Study of the Origin of Hydrogen in Fatty Acids Produced In Vivo in Chicken," *European Journal of Lipid Science and Technology* 108:125-133.

Zhang, Z-Q. et al. (Feb. 1998) "Kinetics of CD4+ T Cell Repopulation of Lymphoid Tissues after Treatment of HIV-1 Infection," *Proc. Natl. Acad. Sci. USA* 95:1154-1159.

Zilversmit, D.B. et al. (1943) "On the Calculation of 'Turnover Time' and 'Turnover Rate' from Experiments Involving the Use of Labeling Agents," *J. of General Physiology* 26(3):325-331.

Backhouse, B. et al. (Mar. 1982). "Effects of haloperidol on cell proliferation in the early postnatal rat brain," *Neuropathology and Applied Neurobiology* 8(2):109-116.

Malberg, J. et al. (Dec. 15, 2000). "Chronic antidepressant treatment increases neurogenesis in adult rat hippocampus," *J Neuroscience* 20(24):9104-9110.

Santarelli, L. et al. (Oct. 8, 2003). "Requirement of hippocampal neurogenesis for the behavioral effects of antidepressants," *Science* 301:805-809.

Whittmann and Heinzle (2001). "Application of MALDI-TOF MS to lysine-producing Corynebacterium glutamicum: a novel approach for metabolic flux analysis," *Eur. J. Biochem.* 268:2441-2455.

Wong, M-L et al. (Jan. 30, 2004). "From monoamines to genomic targets: a paradigm shift for drug discovery in depression," *Nature Reviews: Drug Discovery* 3(2):136-151.

McFarland et al., "Inhibition of DNA synthesis in neonatal rat brain regions caused by acute nicotine administration", Developmental Brain Research, vol. 58, No. 2, Feb. 22, 1991, pp. 223-229.

Ramakers et al., "Chronic suppression of bioelectric activity and cell survival in primary cultures of rat cerebal cortex: biochemical observations", European Journal of Neuroscience, vol. 3, No. 2, Feb. 1991, pp. 154-161.

European Search Report received for EP Patent Application No. 04812281.6, mailed on Oct. 6, 2010, 4 pages.

Hellerstein et al., "Subpopulations of long-lived and short-lived T cells in advanced HIV-1 infection", The Journal of Clinical Investigation, vol. 112, No. 6, Sep. 2003, pp. 956-966.

Siler et al, "De novo lipogenesis, lipid kinetics, and whole-body lipied balances in humans after acute alochol consumption 1-3", The American Journal of Clinical Nutrition, vol. 70, 1999, pp. 928-936.

* cited by examiner

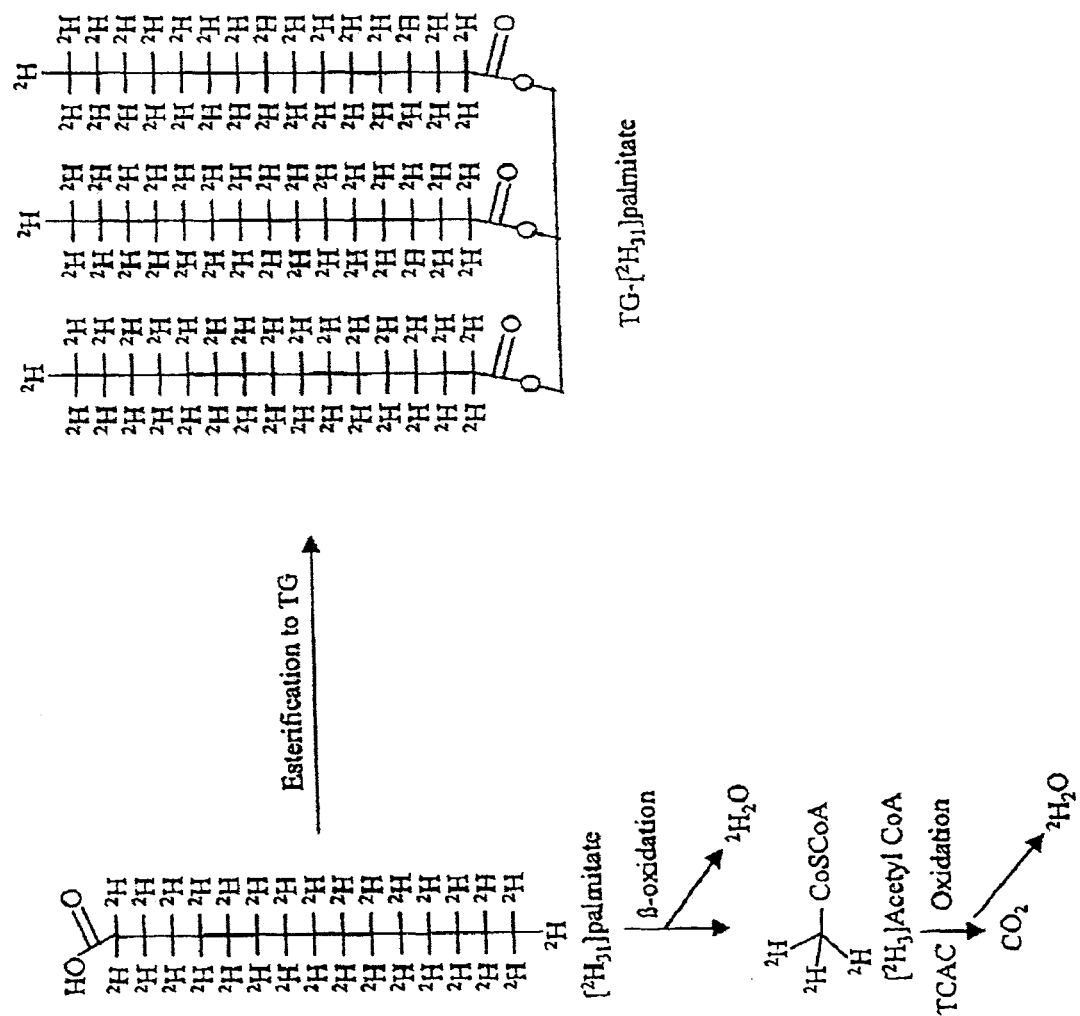
Fig. 1. Fates of $^2H$-attached to fatty acids in cells

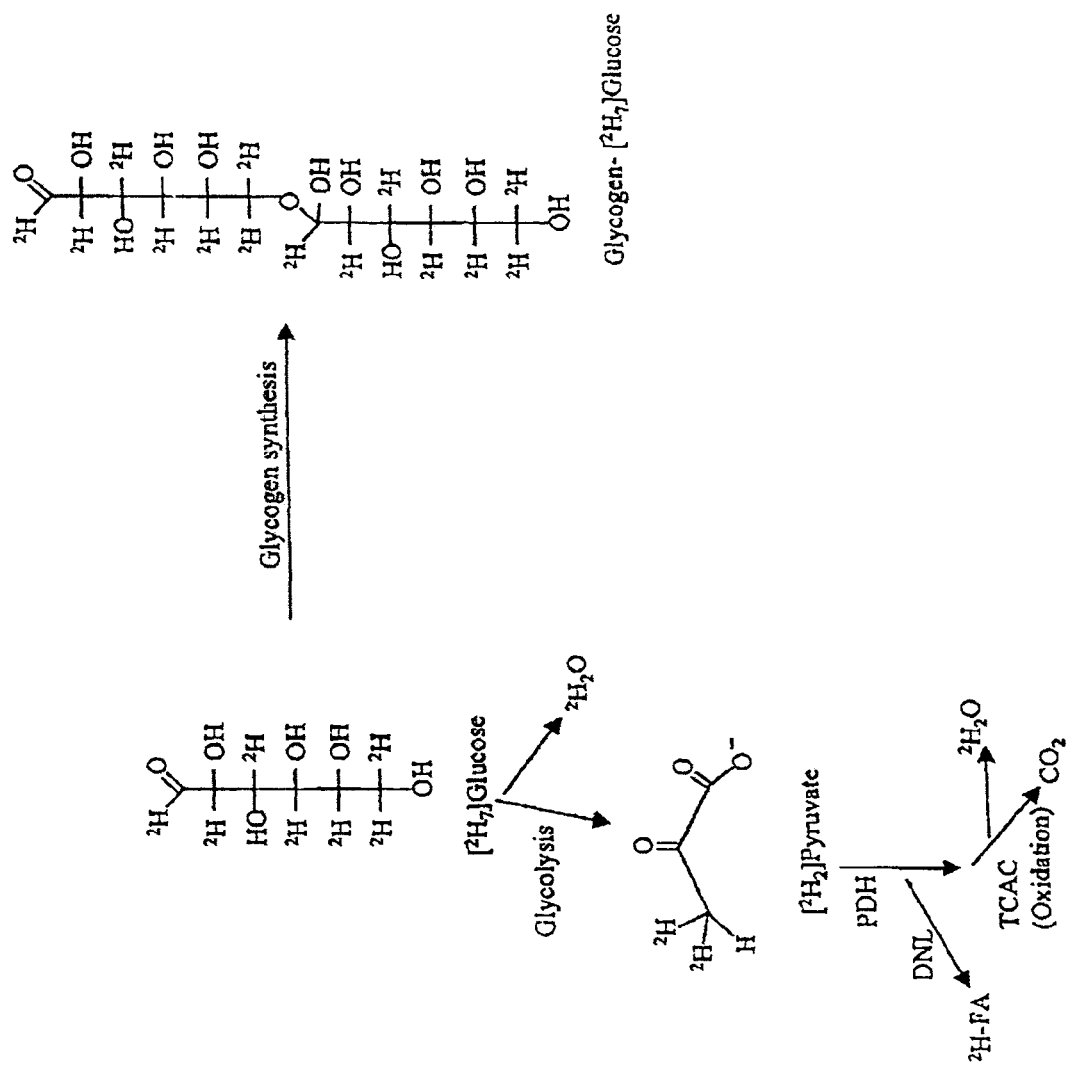
Fig. 2. Fates of $^2$H-attached to glucose in cells

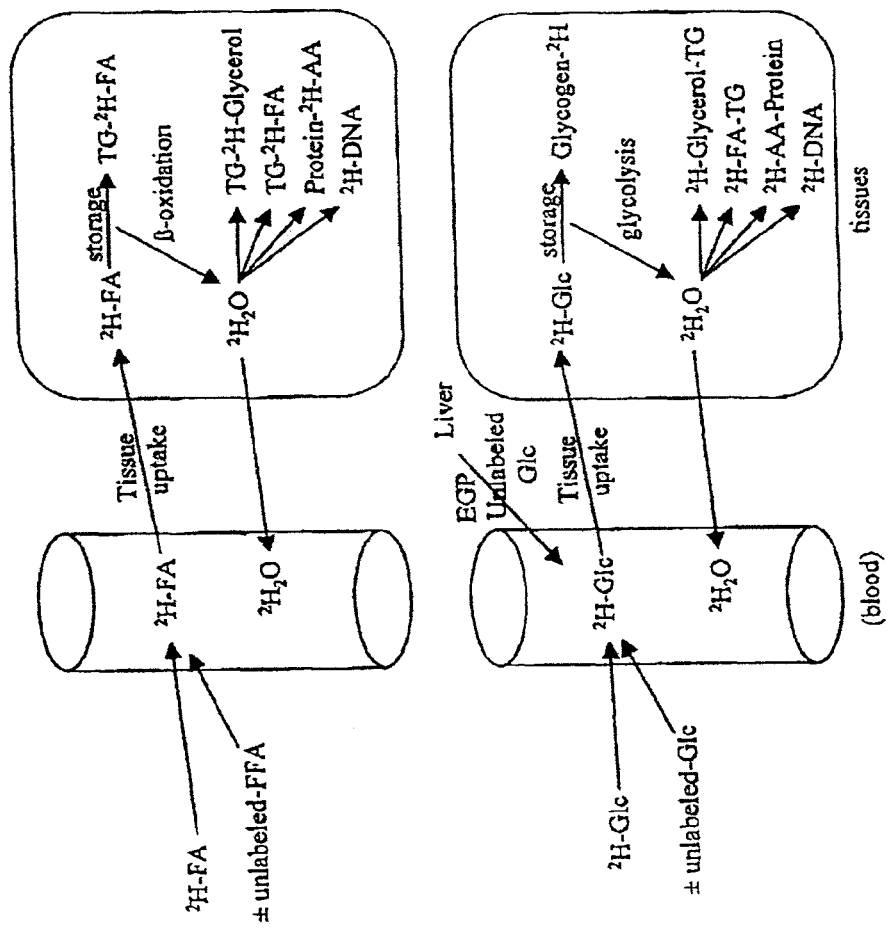
Fig. 3. Schematic model of $^2$H-glucose or $^2$H-FA tolerance test
FA, fatty acid; Glc, glucose; TG, triacylglycerol; AA, amino acid; EGP, endogenous glucose production (liver)

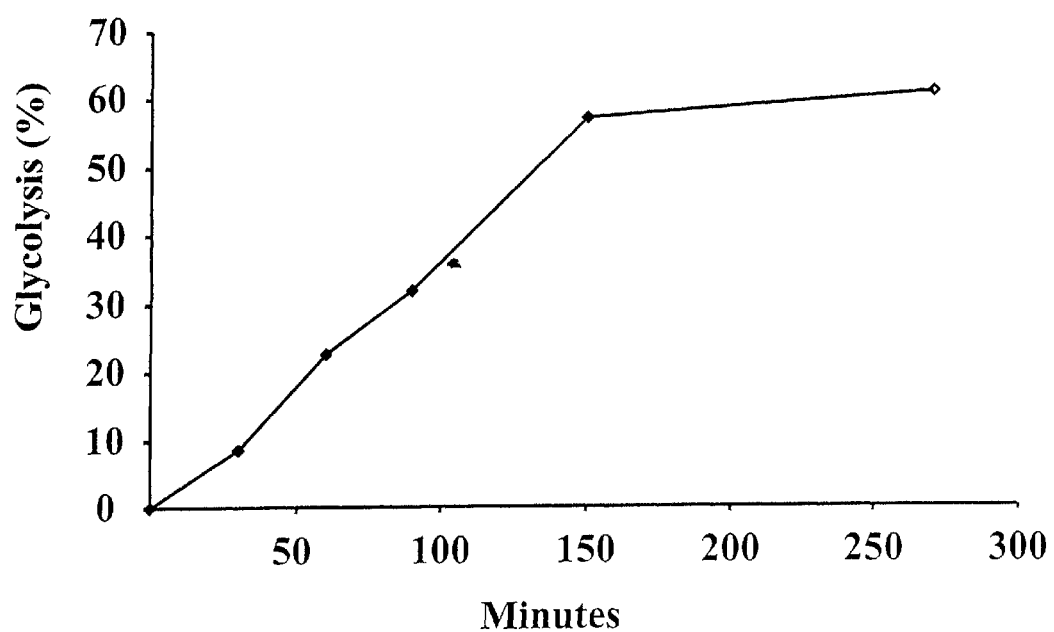
Figure 4: Kinetic Oral Glucose Tolerance Test: Glycolytic disposal of glucose in a Normal Human Subject

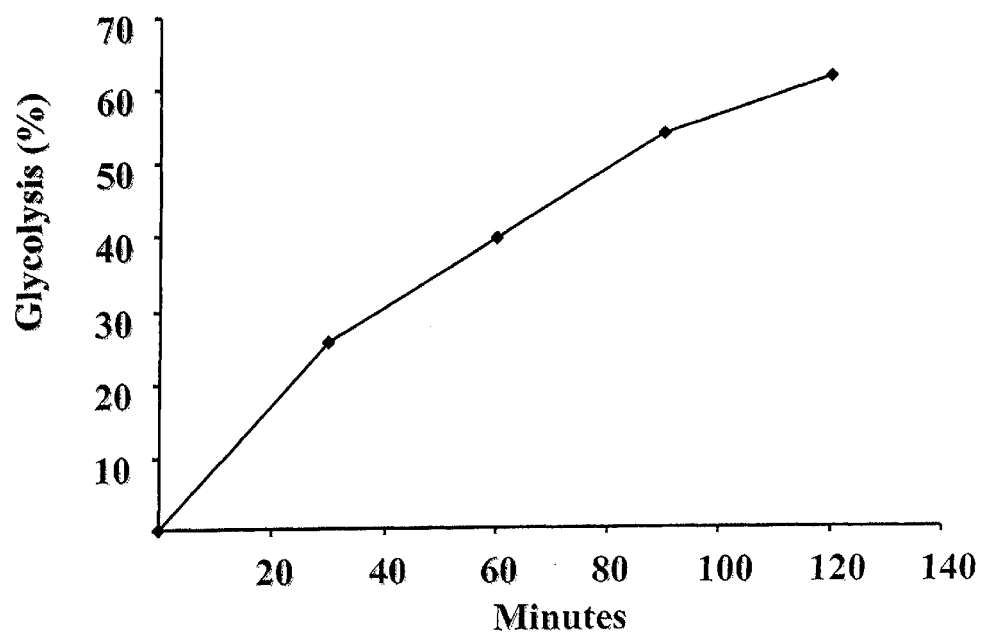
Figure 5: Kinetic Oral Glucose Tolerance Test: Glycolytic disposal of glucose in a Normal Mouse

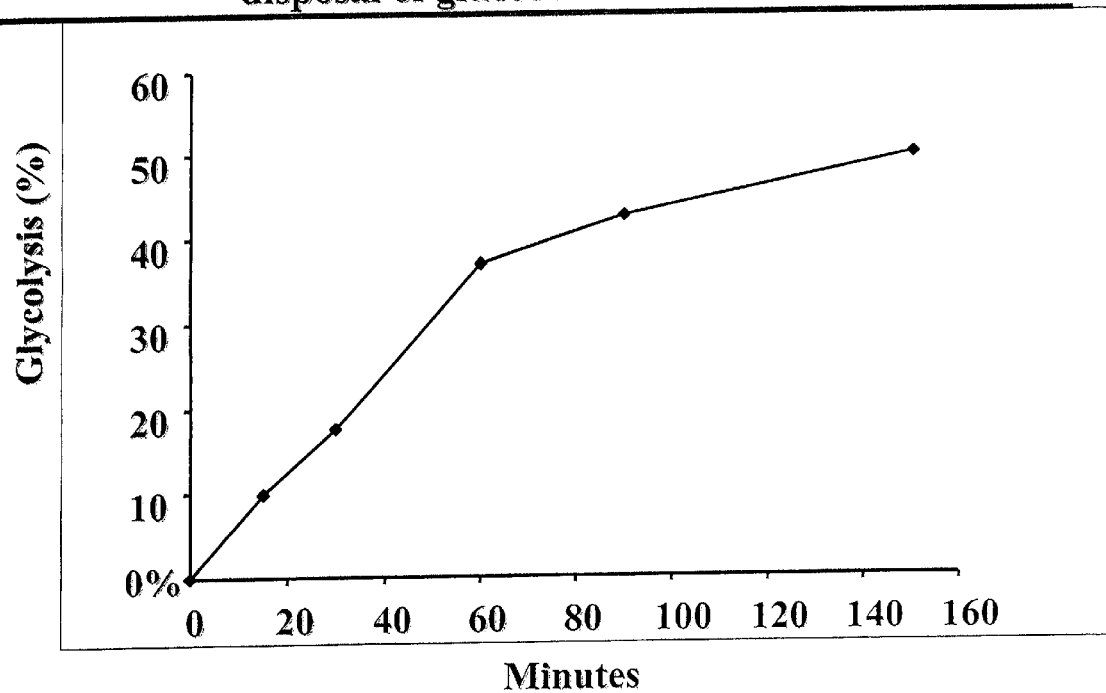
Figure 6: Kinetic Oral Glucose Tolerance Test: glycolytic disposal of glucose in a Normal Rat

METHODS FOR IDENTIFYING THE EFFECT OF A DRUG AGENT ON THE METABOLISM OF SUGARS AND FATS IN AN INDIVIDUAL

RELATED APPLICATION

This application is a Divisional patent application of U.S. patent application Ser. No. 10/701,990, filed Nov. 4, 2003 now U.S. Pat. No. 7,504,233, which claims priority to U.S. Provisional Application Ser. No. 60/423,964, filed Nov. 4, 2002, all of which are hereby incorporated by reference in their entirety.

FIELD OF THE INVENTION

The present invention relates to the field of sugar and fatty acid metabolism. In particular, methods for determining the metabolism of one or more sugars or fatty acids in living organisms, including human subjects, are described.

BACKGROUND OF THE INVENTION

Utilization of nutrients is key to many diseases, including obesity, insulin resistance/diabetes mellitus, hyperlipidemia, and others. The capacity to oxidize dietary fat relative to the tendency to store ingested fat, for example, is considered to be a central determinant of susceptibility to dietary fat-induced obesity. Similarly, the capacity to store or oxidize dietary glucose is a key element in insulin resistance and glucose intolerance/diabetes. Tools for assessing the fate of nutrients in the body in living organisms have lagged behind, however. Currently available tools suffer from many limitations.

The oral glucose tolerance test (OGTT) is widely used in medical research and clinical medicine for assessing insulin sensitivity of tissues. The principle of the OGTT is that uptake of glucose from blood by tissues, along with suppression of release of endogenously produced glucose into blood from tissues, is reflected in the clearance rate of an exogenous glucose load from the bloodstream. This approach is crude, however, and no information is generated about the specific metabolic fate or consequences of the glucose administered. As a result, no information is generated about the mechanisms underlying impaired glucose tolerance. Though widely used in clinical practice, the OGTT is of limited utility.

Fat tolerance testing has a similar basis and similar limitations as OGTT. The fat tolerance test measures the uptake of fatty acids from blood by tissues. This approach is also crude, and gives no information about the specific metabolic fate or consequences of the fat administered. As a result, no information is generated about the mechanisms underlying impaired fat tolerance. Fat tolerance testing has mostly been used to assess the clearance of dietary fat from blood in context of evaluating hyperlipidemia. Fat tolerance testing is not helpful for assessing sensitivity to high fat-induced obesity.

Indirect calorimetry (IC), or the measurement of fuel oxidation based on respiration, is useful for whole body studies. IC, however, is expensive and requires complex equipment for small animal studies. Also, IC only reveals the net oxidation of fuels in the whole body, without revealing more details concerning the fate of individual fuels in the tissues.

Insulin/glucose clamps and other intensive approaches are of limited practical utility in clinical practice or broad-based drug screening/discovery, due to their labor-intensive nature. Physiologic relevance is often also uncertain, since the procedures used (e.g. intravenous glucose infusion at high rates) do not mimic normal physiologic intake of these nutrients.

The most direct approach is by use of isotopic techniques. These have been highly problematic, however. The oxidation of $^{13}$C- or $^{14}$C-labeled glucose or fatty acids to $^{13}CO_2$ or $^{14}CO_2$ has been used as a marker of tissue oxidation (1-3). The references cited herein are listed at the end of the specification before the claims. The serious flaws with this approach have been discussed previously (4). In brief, recovery of labeled $CO_2$ is a highly variable and unreliable index of tissue production of $CO_2$, due to re-utilization/exchange pathways of $^{13}CO_2$ or $^{14}CO_2$. Yield of labeled $CO_2$ generated oxidatively in tissues can be as low as 20%, or as high as 80% (1-4).

The most common risk factor setting for cardiovascular disease is the so-called syndrome X or multiple risk factor syndrome (15) wherein an individual exhibits the combination of obesity, hypertension, hyperlipidemia, and glucose intolerance or diabetes. This syndrome is now widely believed to be tied together pathogenically by insulin resistance, defined as lower-than-normal sensitivity of tissue to the effects of insulin on glucose metabolism (15).

A primary component of tissue insulin resistance is impairment of the efficiency and rate of skeletal muscle and adipose tissue uptake and metabolism of glucose in response to insulin exposure. One component of tissue glucose metabolism is storage as glycogen; the main alternative pathway for glucose metabolism in a tissue is glycolytic metabolism, leading to oxidation or other fates (FIGS. 2 and 3). Both the storage (non-oxidative) and glycolytic (oxidative) pathways are impaired in insulin resistant tissues, such as skeletal muscle (15).

Because the insulin resistance syndrome is so common— indeed is the most common medical abnormality in contemporary Western populations—a reliable laboratory test for diagnosing and monitoring insulin resistance has long been a very high priority. Various commentators have stated that a clinical marker of insulin resistance would be a "holy grail in the fields of modern diabetes and cardiovascular disease" (C. Kahn, M.D., Director of Scientific Sessions, American Diabetes Association, October 2003). The availability of a clinical test for insulin resistance would affect not only patient care but also would allow drugs to be developed specifically to treat insulin resistance.

Unfortunately, no current laboratory test is a reliable measure of insulin resistance. Serum insulin concentrations are highly variable from assay to assay and are influenced by insulin clearance as well as tissue sensitivity to insulin. Other measures, such as blood triglyceride concentration, fasting glucose concentration, oral glucose tolerance, body mass index, waist-to-hip ratio, etc. correlate poorly with clinical insulin sensitivity (as measured by a labor-intensive research test, such as the insulin-glucose clamp technique; see Ref. 15).

A technique for quantifying glucose metabolism by tissues—in particular, glycolysis and/or glycogen storage of a glucose load—would therefore have enormous impact on medical practice and drug trials.

SUMMARY OF THE INVENTION

In order to meet these needs, the present invention is directed to methods of determining the metabolism of one or more sugars or fatty acids, and uses of the methods in diagnosis and testing, and kits for determining the metabolism of one or more sugars and fatty acids.

In one format the invention disclosed herein represents a reliable measure of insulin resistance, and reveals tissue insulin sensitivity or resistance in an individual. Use of the methods disclosed herein allows diagnostic classification of patients (for decisions regarding risk-factor interventions), clinical monitoring of treatments intended to improve insulin sensitivity and reduce insulin resistance (such as the thiazolidinediones or metformin), and clinical development of new agents to treat insulin resistance (as an end-point or biomarker of drug effect).

In one variation, the invention is directed to a method of determining metabolism of one or more sugars or fatty acids in an individual, where the method includes (a) administering one or more compositions of one or more $^2$H-labeled sugars or $^2$H-labeled fatty acids to an individual; (b) obtaining one or more bodily tissues or fluids at one or more times from the individual; and (c) detecting the incorporation of the $^2$H from the $^2$H-labeled sugars or $^2$H-labeled fatty acids into water to determine the sugar or fatty acid metabolism in the individual.

In another variation, the one or more compositions include $^2$H-labeled glucose. In another variation, the one or more compositions include [6,6-$^2$H$_2$]glucose, [1-$^2$H$_1$]glucose, [3-$^2$H$_1$]glucose, [2-$^2$H$_1$]glucose, [5-$^2$H$_1$]glucose, or [1,2,3,4,5,6-$^2$H$_7$]glucose.

In another variation, the one or more compositions are administered orally, by gavage, intraperitoneally, intravenously, or subcutaneously. In a further variation, the one or more compounds are administered orally.

In another variation, the individual is a mammal. In a further variation, the mammal is chosen from humans, rodents, primates, hamsters, guinea pigs, dogs, and pigs. In a still further variation, the mammal is a human.

In another variation, the one or more bodily tissues or fluids are chosen from blood, urine, saliva, and tears. In a further variation, the one or more bodily tissues or fluids are chosen from liver, muscle, adipose, intestine, brain, and pancreas.

In yet another variation, the water may be partially purified. In a further variation, the water may be isolated.

In another variation, the method includes the additional step of measuring $^2$H incorporation into one or more chemical compositions such as glucose, glycogen, glycerol-triglyceride, triglyceride fatty acid, proteins, and DNA. In a further variation, the chemical composition is glucose. In a still further variation the method includes the additional step of measuring endogenous glucose production. In another variation, the method includes the additional step of measuring the proportion of labeled glucose stored in tissue glycogen relative to sugar administered. In yet another variation, the method includes the additional step of measuring the proportion of administered $^2$H-glucose undergoing glycolysis.

In another variation, the chemical composition is glycogen.

In another variation, the chemical composition is glycerol-triglyceride. In yet another variation, the method includes the additional step of calculating new triglyceride synthesis.

In another variation, the chemical composition is triglyceride fatty acid. In still a further variation, the method includes the additional step of calculating new fatty acid synthesis.

In another variation, the method includes the additional step of calculating the proportion of labeled fatty acids stored in tissue relative to labeled fatty acid administered. In a further variation, the method includes the additional step of calculating the proportion of administered labeled fatty acids undergoing fatty acid oxidation.

In another variation, the chemical composition is a protein.

In yet another variation, the chemical composition is DNA. In a further variation, the method includes the additional step of calculating the rate of DNA synthesis.

In another variation, the method of determining sugar or fatty acid metabolism in an individual further includes calculating the rate of incorporation of $^2$H into the water. In another variation, the method includes calculating the rate of incorporation of $^2$H into one or more chemical compositions such as glucose, glycogen, glycerol-triglyceride, triglyceride fatty acid, proteins, and DNA. Optionally, both the rates of water formation and chemical composition formation may be monitored.

In another variation, the water may be detected by gas chromatography/mass spectrometry, liquid chromatography-mass spectrometry, gas chromatography-pyrolysis-isotope ratio/mass spectrometry, or gas chromatography-combustion-isotope ratio/mass spectrometry, cycloidal mass spectrometry, Fourier-transform-isotope ratio (IR)-spectroscopy, near IR laser spectroscopy, or isotope ratio mass spectrometry.

In a still further variation, the detecting step may be accomplished by detecting one part $^2$H in $10^7$ parts water.

In another aspect, the invention also includes further applications of the methods of the invention to determine the metabolism of sugars and fatty acids. In one variation, a drug agent is introduced to the individual prior to determining the metabolism of one or more sugars or fatty acids, and the effect on an individual is subsequently identified. In another variation, the metabolism determinations are used as a surrogate marker for FDA or other regulatory agency approval of drugs. In yet another variation, the metabolism determination is used for the clinical management of patients. In still a further variation, the metabolism determination includes diagnosing, prognosing, or identifying individuals at risk for insulin resistance/diabetes mellitus in the individual. In another variation, the metabolism determination includes diagnosing, or identifying individuals at risk for, high-fat diet-induced obesity. In still another variation, the metabolism determination includes monitoring the effects of interventions to prevent or reverse insulin resistance/diabetes mellitus or high-fat diet-induced obesity. In another variation, the metabolism determination includes diagnosing or treating wasting disorders, hypoglycemia, or glycogen storage disease.

The invention is also directed to drug agents that are identified as having an effect on the sugar or fatty acid metabolism of the individual, and isotopically perturbed molecules such as glucose, glycogen, glycerol-triglyceride, triglyceride fatty acid, proteins, and DNA.

The invention is further directed to a kit for determining the metabolism of a sugar in an individual. The kit may include one or more labeled sugars and instructions for use of the kit. The kit is useful for determining sugar metabolism in an individual. The kit may further include chemical compounds for isolating water. The kit may also include chemical compounds for isolating glucose, glycogen, proteins or DNA. The kit may also include a tool for administering labeled glucose. The kit may further include an instrument for collecting a sample from the individual.

The invention is further directed to a drug agent the effect of which was at least partially identified by the methods of the invention.

The invention is further directed to an isotopically perturbed molecule chosen from glycogen, glycerol-triglyceride, triglyceride fatty acid, proteins, and DNA.

The invention is further directed to a method of manufacturing one or more drug agents at least partially identified by the methods of the invention.

The invention is further directed to an information storage device including data obtained from the methods of the invention. The device may be a printed report or a computer. The printed report may be printed on paper, plastic, or microfiche. The device may be a computer disc. The computer disk may be chosen from a compact disc, a digital video disc, and a magnetic disc.

BRIEF DESCRIPTION OF THE DRAWINGS

FIG. 1 depicts the fate of $^2$H attached to fatty acids in the cells. In this case, palmitate is shown. The fatty acid is metabolized via β-oxidation to release hydrogen atoms from C—H bonds of fats to body $H_2O$. Alternatively, fatty acids may be esterified to produce triglyceride-fatty acids, in this case triglyceride-palmitate.

FIG. 2 depicts the fate of $^2$H attached to sugars, in this case glucose. Sugars are metabolized via glycolysis and the citric acid cycle to release hydrogen atoms from C—H bonds of sugars to body $H_2O$. Alternatively, glucose may form glycogen.

FIG. 3 depicts a schematic molecule of glucose or fat tolerance tests. Glucose or fatty acid metabolism may be measured directly from release of $^2$H to body water. Measurements may include the additional step of incorporating $^2$H from body water back into other labeled chemical compounds, including labeled glycerol-triglycerides, fatty acid-triglycerides, proteins, DNA, or components thereof.

FIG. 4 depicts a kinetic oral glucose tolerance test in a normal human subject. The percent glycolysis, measured by deuterium incorporation into water following administration of deuterium-labeled glucose, is shown over a period of time.

FIG. 5 depicts a kinetic oral glucose tolerance test in a normal mouse. The percent glycolysis, measured by deuterium incorporation into water following administration of deuterium-labeled glucose, is shown over a period of time.

FIG. 6 depicts a kinetic oral glucose tolerance test in a normal rat. The percent glycolysis, measured by deuterium incorporation into water following administration of deuterium-labeled glucose, is shown over a period of time.

DETAILED DESCRIPTION OF THE INVENTION

A method for determining the metabolism of H-labeled sugars and fatty acids is described herein. The methods have numerous applications in the fields of medical diagnostics and biological research.

I. General Techniques

The practice of the present invention will employ, unless otherwise indicated, conventional techniques of molecular biology (including recombinant techniques), microbiology, cell biology, biochemistry, immunology, protein kinetics, and mass spectroscopy, which are within the skill of the art. Such techniques are explained fully in the literature, such as, *Molecular Cloning: A Laboratory Manual*, second edition (Sambrook et al., 1989) Cold Spring Harbor Press; *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney, ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Methods in Enzymology* (Academic Press, Inc.); *Handbook of Experimental Immunology* (D. M. Weir and C. C. Blackwell, eds.); *Gene Transfer Vectors for Mammalian Cells* (J. M. Miller and M. P. Calos, eds., 1987); *Current Protocols in Molecular Biology* (F. M. Ausubel et al., eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); and *Mass isotopomer distribution analysis at eight years: theoretical, analytic and experimental considerations* by Hellerstein and Neese (*Am J Physiol* 276 (*Endocrinol Metab.* 39) E1146-E1162, 1999). Furthermore, procedures employing commercially available assay kits and reagents will typically be used according to manufacturer-defined protocols unless otherwise noted.

II. Definitions

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, *Mass isotopomer distribution analysis at eight years: theoretical, analytic and experimental considerations* by Hellerstein and Neese (*Am J Physiol* 276 (*Endocrinol Metab.* 39) E1146-E1162, 1999), herein incorporated by reference. As appropriate, procedures involving the use of commercially available kits and reagents are generally carried out in accordance with manufacturer defined protocols and/or parameters unless otherwise noted.

"Metabolism" is used interchangeably with "metabolic fate" and "metabolic consequences," and refers generally to biosynthesis, breakdown, conversion, oxidation, and/or reduction of sugars and fatty acids.

"Isotopes" refer to atoms with the same number of protons and hence of the same element but with different numbers of neutrons (e.g., Hydrogen (H) vs. Deuterium (D)). D is also represented as $^2$H, as is common in the art.

"Isotopomers" refer to isotopic isomers or species that have identical elemental compositions but are constitutionally and/or stereochemically isomeric because of isotopic substitution, as for $CH_3NH_2$, $CH_3NHD$ and $CH_2DNH_2$.

"Isotopologues" refer to isotopic homologues or molecular species that have identical elemental and chemical compositions but differ in isotopic content (e.g., $CH_3NH_2$ vs. $CH_3NHD$ in the example above). Isotopologues are defined by their isotopic composition, therefore each isotopologue has a unique exact mass but may not have a unique structure. An isotopologue is usually included of a family of isotopic isomers (isotopomers) which differ by the location of the isotopes on the molecule (e.g., $CH_3NHD$ and $CH_2DNH_2$ are the same isotopologue but are different isotopomers).

"Mass isotopomer" refers to a family of isotopic isomers that are grouped on the basis of nominal mass rather than isotopic composition. A mass isotopomer may comprise molecules of different isotopic compositions, unlike an isotopologue (e.g., $CH_3NHD$, $^{13}CH_3NH_2$, $CH_3^{15}NH_2$ are part of the same mass isotopomer but are different isotopologues). In operational terms, a mass isotopomer is a family of isotopologues that are not resolved by a mass spectrometer. For quadrupole mass spectrometers, this typically means that mass isotopomers are families of isotopologues that share a nominal mass. Thus, the isotopologues $CH_3NH_2$ and $CH_3NHD$ differ in nominal mass and are distinguished as being different mass isotopomers, but the isotopologues $CH_3NHD$, $CH_2DNH_2$, $^{13}CH_3NH_2$, and $CH_3{}^{15}NH_2$ are all of the same nominal mass and hence are the same mass isotopomers. Each mass isotopomer is therefore typically composed of more than one isotopologue and has more than one exact mass. The distinction between isotopologues and mass isotopomers is useful in practice because all individual isotopologues are not resolved using quadrupole mass spectrometers and may not be resolved even using mass spectrometers that produce higher mass resolution, so that calculations from mass spectrometric data must be performed on the abundances of mass isotopomers rather than isotopologues. The mass isotopomer lowest in mass is represented as $M_0$; for most organic molecules, this is the species containing all $^{12}C$, $^1H$, $^{16}O$, $^{14}N$, etc. Other mass isotopomers are distinguished by their mass differences from $M_0$ ($M_1$, $M_2$, etc.). For a given mass isotopomer, the location or position of isotopes within the molecule is not specified and may vary (i.e., "positional isotopomers" are not distinguished).

"Mass isotopomer pattern" refers to a histogram of the abundances of the mass isotopomers of a molecule. In one embodiment, the pattern is presented as percent relative abundances where all of the abundances are normalized to that of the most abundant mass isotopomer; the most abundant isotopomer is said to be 100%. In another embodiment, the form for applications involving probability analysis is proportion or fractional abundance, where the fraction that each species contributes to the total abundance is used (see below). The term isotope pattern is sometimes used in place of mass isotopomer pattern, although technically the former term applies only to the abundance pattern of isotopes in an element.

An "individual" refers to a vertebrate animal including a mammal and further including a human.

A "biological sample" encompasses a variety of sample types obtained from an individual. The definition encompasses blood and other liquid samples of biological origin, that are accessible from an individual through sampling by minimally invasive or non-invasive approaches (e.g., urine collection, blood drawing, needle aspiration, and other procedures involving minimal risk, discomfort or effort). The definition also includes samples that have been manipulated in any way after their procurement, such as by treatment with reagents, solubilization, or enrichment for certain components, such as proteins or polynucleotides. The term "biological sample" also encompasses a clinical sample such as serum, plasma, other biological fluid, or tissue samples, and also includes cells in culture, cell supernatants and cell lysates.

"Biological fluid" includes but is not limited to urine, blood, blood serum, amniotic fluid, interstitial fluid, edema fluid, saliva, lacrimal fluid, inflammatory exudates, synovial fluid, abscess, empyema or other infected fluid, cerebrospinal fluid, sweat, pulmonary secretions (sputum), seminal fluid, feces, bile, intestinal secretions, conjunctival fluid, tears, vaginal fluid, stool, or other bodily fluid.

"Sugar" refers to a monosaccharide or a polysaccharide comprised of monosaccharide residues. Examples of monosaccharides include, but are not limited to, glucose (both D-glucose and L-glucose), mannose, fructose galactose and sugar derivatives such as glucoronic acid, glucosamine. Examples of polysaccharides include, but are not limited to, disaccharides such as sucrose, maltose and lactose and longer chain sugar molecules such as glycogen.

"Labeled sugar" refers to a sugar incorporating one or more $^2H$ isotopes.

"Labeled fatty acid" refers to a fatty acid incorporating one or more $^2H$ isotopes. "Deuterated water" refers to water incorporating one or more $^2H$ isotopes. "Labeled glucose" refers to glucose labeled with one or more $^2H$ isotopes. Specific examples of labeled glucose or $^2H$-labeled glucose include [6,6-$^2H_2$]glucose, [1-$^2H_1$]glucose, and [1,2,3,4,5,6-$^2H_7$]glucose.

"Partially purifying" refers to methods of removing one or more components of a mixture of other compounds. For example, "partially purifying one or more proteins or peptides" refers to removing one or more proteins or peptides from a mixture of one or more proteins or peptides or other compounds. As another example, "partially purifying water" refers to removing one or more molecules, such as macromolecules, types of macromolecules, or salts, from water.

"Isolating" refers to separating one compound from a mixture of compounds. For example, "isolating one or more proteins or peptides" refers to separating one protein or peptide from a mixture of one or more proteins or peptides or other compounds. "Isolating water" refers to removing all additional compounds beyond trace levels from water.

"Drug agent," "pharmaceutical agent," "pharmacological agent," and "pharmaceutical" are used interchangeably to refer to any chemical entities, known drug or therapy, approved drug or therapy, biological agent (e.g., gene sequences, poly or monoclonal antibodies, cytokines, and hormones). Drug agents include, but are not limited to, any chemical compound or composition disclosed in, for example, the 13th Edition of *The Merck Index* (a U.S. publication, Whitehouse Station, N.J., USA), incorporated herein by reference in its entirety.

"Isotopically perturbed" refers to the state of an element or molecule that results from the explicit incorporation of an element or molecule with a distribution of isotopes that differs from the distribution that is most commonly found in nature, whether a naturally less abundant isotope is present in excess (enriched) or in deficit (depleted).

"At least partially identified" in the context of drug discovery and development means at least one clinically relevant pharmacological characteristic of a drug agent has been identified using one or more of the methods of the present invention. This characteristic may be a desirable one, for example, increasing or decreasing molecular flux rates through a metabolic pathway that contributes to a disease process, altering signal transduction pathways or cell surface receptors that alter the activity of metabolic pathways relevant to a disease, inhibiting activation of an enzyme and the like. Alternatively, a pharmacological characteristic of a drug agent may be an undesirable one for example, the production of one or more toxic effects. There are a plethora of desirable and undesirable characteristics of drug agents well known to those skilled in the art and each will be viewed in the context of the particular drug agent being developed and the targeted disease. Of course, a drug agent can be more than at least partially identified when, for example, when several characteristics have been identified (desirable or undesirable or both) that are sufficient to support a particular milestone decision point along the drug development pathway. Such milestones include, but are not limited to, pre-clinical decisions for in vitro to in vivo transition, pre-IND filing go/no go decision, phase I to phase II transition, phase II to phase III transition, NDA filing, and FDA approval for marketing. Therefore, "at least partially" identified includes the identification of one or more pharmacological characteristics useful in evaluating a drug agent in the drug discovery/drug development process. A pharmacologist or physician or other researcher may evaluate all or a portion of the identified desirable and undesirable characteristics of a drug agent to establish its therapeutic index. This may be accomplished using procedures well known in the art.

"Manufacturing drug agents" in the context of the present invention includes any means, well known to those skilled in the art, employed for the making of a drug agent product. Manufacturing processes include, but are not limited to, medicinal chemical synthesis (i.e., synthetic organic chemistry), combinatorial chemistry, biotechnology methods such as hybridoma monoclonal antibody production, recombinant DNA technology, and other techniques well known to the skilled artisan. Such a product may be a final drug agent that is marketed for therapeutic use, a component of a combination product that is marketed for therapeutic use, or any intermediate product used in the development of the final drug agent product, whether as part of a combination product or a single product.

"Elevated risk" is used interchangeably herein with "increased risk" and means an increase, beyond measurable background levels, of the risk of an individual for acquiring a condition or disease based on the presence or absence of one or more risk factors.

"Risk factor" as used herein, means an external or internal factor that is associated with a disease or disorder. A risk factor may reflect an aspect of causation, whether direct or indirect, but is not so limited. A risk factor may have an association with the onset of a disease or disorder and may be predictive of such (i.e., a marker of disease), but may or may not be an indicator of the underlying pathology of the disease or disorder.

III. Methods of the Invention

Non-invasive tests for determining the metabolism of metabolites such as sugars and fatty acids in the body have great utility for clinical diagnostics and biomedical research. We disclose here methods that allow high-throughput, inexpensive and simple measurements of the disposal pathways and metabolic consequences of sugars and fatty acids in living organisms, including humans. As used herein "metabolism," "metabolic fate" and "metabolic consequences" are used interchangeably and refer generally to biosynthesis, breakdown, conversion, oxidation, and/or reduction of sugars or fatty acids upon administration. The test involves determining the metabolism of sugars and fatty acids by administering one or more isotope labeled sugars or labeled fatty acids to an individual, then detecting the release of the label in bodily tissues or fluids to determine the metabolism of the one or more sugars or fatty acids in the individual. In one embodiment, the test involves administration of deuterium-labeled glucose or fatty acids to a human subject or experimental animal, then measurement of the release of deuterium to body water. Highly sensitive measurements of label enrichments in chemical compositions contained in the bodily tissues or fluids allow great sensitivity and accuracy by this approach.

The tests disclosed herein have utility as drug discovery tools (e.g., for identifying genes and drugs that alter tissue glucose or fat utilization pathways); as surrogate biomarkers for FDA approval of drugs (e.g., agents influencing fat oxidation or insulin sensitivity of tissues); and as diagnostic measures for the clinical management of patients. The methods may be used to diagnose, or identify, the risk of insulin resistance or diabetes mellitus. The methods may also be used to identify diet-induced obesity or the risk of acquiring diet-induced obesity. The methods may further be used to diagnose or treat wasting diseases and disorders. Further, the methods may also be used to identify hypoglycemia or hyperglycemia. In addition, the methods may be used to diagnose or treat glycogen storage diseases. By measuring the total disappearance of glucose ($D_{glucose}$) and the formation of glycolysis (as described, infra), the rate of glycogen synthesis and/or the concentration (i.e., the amount) of glycogen synthesized (i.e., formed) can then be determined. Knowing the rate of glycogen synthesis and/or the amount of glycogen formed, for example, enables the clinician to evaluate the efficacy of drug agents intended to improve tissue insulin sensitivity (e.g., in pre-diabetic individuals) or in treating glycogen storage diseases. Alternatively, knowing the rate of glycogen synthesis and/or the amount of glycogen formed allows the clinician to more accurately diagnose or prognose a glycogen storage disease. Additionally, the rate of glycogen synthesis and/or the amount of glycogen formed is a well-accepted early marker for an elevated risk of developing cardiovascular disease or insulin-resistant disorders such as type II diabetes.

The invention disclosed herein combines the simplicity of an OGTT or fat tolerance test with the precision, accuracy and metabolic specificity of deuterium tracing. Partitioning labeled $^2H$, attached to specific C—H bonds of administered compounds such as sugars or fatty acids, can reveal the specific metabolic fate of the nutrient in a living organism and can be monitored in a high-throughput, inexpensive manner.
Methods of Determining the Metabolism of Compositions Containing Sugars or Fatty Acids in an Individual
  i) Administering Labeled Metabolites to an Individual
    a. Compositions Containing Sugars
Compositions containing sugars may include monosaccharides, polysaccharides, or other compounds that are covalently bonded to monosaccharides or polysaccharides.

$^2H$-labeled sugars may be administered to an individual as monosaccharides or as polymers of monosaccharide residues. Labeled monosaccharides may be readily obtained commercially (for example, Cambridge Isotopes, Massachusetts).

Relatively low quantities of compositions that contain $^2H$-labeled sugars need to be administered. Quantities may be on the order of milligrams, $10^1$ mg, $10^2$ mg, $10^3$ mg, $10^4$ mg, $10^5$ mg, or $10^6$ mg. $^2H$-labeled sugar enrichment may be maintained for weeks or months in humans and in animals without any evidence of toxicity. The lower cost of commercially available labeled monosaccharides, and low quantity that need to be administered, allow maintenance of enrichments at low expense.

In one particular variation, the labeled sugar is glucose. FIG. 2 shows the fate of $^2H$-labeled glucose. Glucose is metabolized by glycolysis and the citric acid cycle. Glycolysis releases most of the H-atoms from C—H bonds of glucose; oxidation via the citric acid cycle ensures that all H-atoms are released to $H_2O$. In a further variation, the labeled glucose may be $[6,6-^2H_2]$glucose, $[1-^2H_1]$glucose, and $[1,2,3,4,5,6-^2H_7]$glucose.

In another variation, labeled sugar may be fructose or galactose. Fructose is metabolized via the fructose 1-phosphate pathway, and secondarily through phosphorylation to fructose 6-phosphate by hexokinase. Galactose is metabolized via the galactose to glucose interconversion pathway.

Any other sugar may be utilized in the disclosed methods. Other monosaccharides, include, but are not limited to, trioses, pentoses, hexose, and higher order monosaccharides. Monosaccharides further include, but are not limited to, aldoses and ketoses.

In another variation, compositions containing polysaccharides may be administered. The polymers may be formed from monosaccharides. For example, labeled glycogen, a polysaccharide, is formed by glucose residues. In another variation, labeled polysaccharides may be administered. As further variation, labeled sugar monomers may be administered as a component of sucrose (glucose α-(1,2)-fructose), lactose (galactose β-(1,4)-glucose), maltose (glucose α-(1, 4)-glucose), starch (glucose polymer), or other polymers.

In another variation, the labeled sugar may be administered orally, by gavage, intraperitoneally, intravascularly including intra-arterially and intravenously, subcutaneously, or other bodily routes. In particular, the sugars may be administered to an individual orally, optionally as part of a food or drink. By "administering" or "administration" is meant any method that introduces the labeled sugar to, in or on an individual.

The individual may be a mammal. In one embodiment, the individual may be an experimental mammal. In another embodiment, the individual may be a rodent, primate, hamster, guinea pig, dog, or pig. In yet another embodiment, the individual may be a human.

b. Labeled Fatty Acids

Determining the metabolism of compounds that contain $^2$H-labeled fatty acids is also included in this invention.

$^2$H-labeled fatty acids may be administered to an individual as fats or other compounds containing the labeled fatty acids. $^2$H-labeled fatty acids may be readily obtained commercially. Relatively low quantities of labeled fatty acids need to be administered. Quantities may be on the order of milligrams, $10^1$ mg, $10^2$ mg, $10^3$ mg, $10^4$ mg, $10^5$ mg, or $10^6$ mg. Fatty acid enrichment, particularly with $^2$H, may be maintained for weeks or months in humans and in animals without any evidence of toxicity. The lower cost of commercially available labeled fatty acids, and low quantity that need to be administered, allow maintenance of enrichments at low expense.

FIG. 1 shows the fate of $^2$H-labeled fatty acids during β-oxidation (metabolism) of fatty acids in cells. β-oxidation releases hydrogen atoms from C—H bonds of fats to body $H_2O$. All H-atoms are released from $^2$H-fatty acids during β-oxidation and, once β-oxidation starts on a fatty acid, the process goes to completion. The release of labeled fatty acids, particularly $^2$H-fatty acid, to labeled water, particularly $^2H_2O$, accurately reflects fat oxidation. Administration of modest amounts of labeled-fatty acid is sufficient to measure release of labeled hydrogen or oxygen to water. In particular, administration of modest amounts of $^2$H-fatty acid is sufficient to measure release of H to deuterated water (i.e., $^2H_2O$).

Relatively low quantities of labeled fatty acid or fatty acid residue need to be administered. Quantities may be on the order of milligrams, $10^1$ mg, $10^2$ mg, $10^3$ mg, $10^4$ mg, $10^5$ mg, or $10^6$ mg. $^2$H-labeled fatty acid enrichment may be maintained for weeks or months in humans and in animals without any evidence of toxicity. The lower expense of commercially available labeled fatty acids and fatty acid residues, and low quantity that need to be administered, allow maintenance of enrichments at low expense.

In another variation, the labeled fatty acids may be administered orally, by gavage, intraperitoneally, intravascularly including intra-arterially and intravenously, subcutaneously, or other bodily routes. In particular, the labeled fatty acids may be administered to an individual orally, optionally as part of a food or drink. By "administering" or "administration" is meant any method that introduces the labeled fatty acid to, in or on an individual.

The individual may be a mammal. In one embodiment, the individual may be an experimental mammal. In another embodiment, the individual may be a rodent, primate, hamster, guinea pig, dog, or pig. In yet another embodiment, the individual may be a human.

(ii) Obtaining One or More Bodily Tissues or Fluids from Said Individual

A biological sample is obtained from bodily tissues or fluids of an individual. Specific methods of obtaining biological samples are well known in the art. Bodily fluids include, but are not limited to, urine, blood, blood serum, amniotic fluid, spinal fluid, conjunctival fluid, saliva, tears, vaginal fluid, stool, seminal fluid, and sweat. The fluids may be isolated by standard medical procedures known in the art. Bodily tissues include, but are not limited to, liver, muscle, adipose, intestine, brain, and pancreas.

In one variation, water may be partially purified. In another variation, the water may be isolated.

In another variation, the one or more bodily tissue or fluids may be obtained after a period of time. In a further variation, the one or more bodily tissues or fluids may be obtained multiple times.

iii) Detecting the Incorporation of $^2$H into Water a. Mass Spectrometry

The isotope label, or alternatively, the labeled chemical compositions, may be determined by various methods such as mass spectrometry, particularly gas chromatography-mass spectrometry (GC-MS). Incorporation of labeled isotopes into chemical compositions may be measured directly. Alternatively, incorporation of labeled isotopes may be determined by measuring the incorporation of labeled isotopes into one or more hydrolysis or degradation products of the chemical composition. The hydrolysis or degradation products may optionally be measured following either partial purification or isolation by any known separation method, as described previously.

Mass spectrometers convert components of a sample into rapidly moving gaseous ions and separate them on the basis of their mass-to-charge ratios. The distributions of isotopes or isotopologues of ions, or ion fragments, may thus be used to measure the isotopic enrichment in one or more chemical compositions, or chemical or biochemical degradation products.

Generally, mass spectrometers comprise an ionization means and a mass analyzer. A number of different types of mass analyzers are known in the art. These include, but are not limited to, magnetic sector analyzers, electrostatic analyzers, quadrupoles, ion traps, time of flight mass analyzers, and fourier transform analyzers. In addition, two or more mass analyzers may be coupled (MS/MS) first to separate precursor ions, then to separate and measure gas phase fragment ions.

Mass spectrometers may also include a number of different ionization methods. These include, but are not limited to, gas phase ionization sources such as electron impact, chemical ionization, and field ionization, as well as desorption sources, such as field desorption, fast atom bombardment, matrix assisted laser desorption/ionization, and surface enhanced laser desorption/ionization.

In addition, mass spectrometers may be coupled to separation means such as gas chromatography (GC) and high performance liquid chromatography (HPLC). In gas-chromatography mass-spectrometry (GC/MS), capillary columns from a gas chromatograph are coupled directly to the mass spectrometer, optionally using a jet separator. In such an application, the gas chromatography (GC) column separates sample components from the sample gas mixture and the separated components are ionized and chemically analyzed in the mass spectrometer.

Various mass spectrometers and combinations of separation technologies and mass spectrometers are contemplated for use in the invention including, but not limited to, gas chromatography/mass spectrometry, liquid chromatography-mass spectrometry, gas chromatography-Pyrolysis-isotope ratio/mass spectrometry, or gas chromatography-combustion-isotope ratio/mass spectrometry, cycloidal mass spectrometry, Fourier-transform-isotope ratio (IR)-spectroscopy, near IR laser spectroscopy, or isotope ratio mass spectrometry b. Metabolism Very low quantities of labeled water may be detected. In one embodiment, 1 part in $10^3$ labeled water may be identified. In another embodiment, 1 part in $10^4$ labeled water may be identified. In another embodiment, 1 part in $10^5$ labeled water may be identified. In another embodiment, 1 part in $10^6$ labeled water may be identified. In another embodiment, 1 part in $10^7$ labeled water may be identified.

1. Detecting Water Following Sugar Metabolism

The methods of measuring the consequences of sugar ingestion may be accomplished by measuring sugar metabolism products. The rate of metabolic water production from the oxidation of fuels, including sugars, is sufficient to achieve relatively high levels of labeled water when modest doses of compounds containing labeled sugars are administered.

Alternatively, labeled glucose may be polymerized to form labeled glycogen, which may then be measured.

2. Detecting Water Following Fatty Acid Metabolism

The methods of measuring the consequences of fatty acid ingestion may be accomplished by measuring fatty acid metabolism products. The rate of metabolic water production from fatty acid oxidation (metabolism) is sufficient to achieve relatively high levels of labeled water, particularly $^2H_2O$, when modest doses of labeled fatty acids or compounds containing fatty acid residues are administered.

FIG. 3 depicts the fatty acid metabolism pathway using deuterium $^2H$-labeled fatty acids. Fatty acids ingested by an individual are delivered to tissues, optionally stored as triacylglycerol, or converted to water by β-oxidation. Labeled water may then be returned to the blood stream, and incorporated into bodily fluids.

Labeled water may then be detected to determine the degree of label incorporation.

iv) The Additional Step of Measuring $^2H$ Incorporated into One or More Chemical Compositions The invention also contemplates the additional step of measuring $^2H$ incorporated into one or more chemical compositions in addition to water. Incorporation of labeled water generated from either labeled glucose or labeled fatty acid metabolism, can be used to measure other synthesis and storage pathways in an organism (FIGS. 1 and 2). These pathways include protein synthesis, lipid synthesis (triglyceride synthesis and cholesterogenesis), new fat synthesis (de novo lipogenesis), and DNA synthesis (cell proliferation). The addition of these supplemental measurements (FIG. 3) adds further information to the $^2H$-fatty acid or $^2H$-glucose labeling strategies.

One or more chemical compositions may be obtained, and optionally partially purified or isolated, from the biological sample using standard biochemical methods known in the art. Chemical compositions include, but are not limited to, glucose, glycogen, glycerol-triglyceride, triglyceride fatty acid, proteins, and DNA. Optionally, fragments of the compositions may also be obtained. The frequency of biological sampling can vary depending on different factors. Such factors include, but are not limited to, the nature of the chemical composition tested, ease of sampling, and half-life of a drug used in a treatment if monitoring responses to treatment.

In one variation, the one or more chemical compositions may be glucose. In a further variation, the dilution of orally administered labeled sugars, particularly $^2H$-glucose, in plasma glucose load reveals endogenous glucose production (EGP, FIG. 3). Considerable information can be gained about glucose utilization and synthesis pathways in the body by use of this approach. FIG. 3 depicts the glucose metabolism pathway, specifically for deuterium labeled glucose. Glucose ingested by an individual is delivered to tissues, optionally stored as glycogen, or converted to water and carbon dioxide via glycolysis and the citric acid cycle. Labeled water, particularly $^2H_2O$, may then be returned to the blood stream, and incorporated into bodily fluids, then into biosynthetic products. In a still further variation, the proportion of glucose may be used to identify the proportion of administered $^2H$-labeled glucose undergoing glycolysis.

In another variation, the method may be used to determine newly synthesized glycogen. Newly synthesized glycogen can be determined indirectly by subtracting glycolysis from the total amount of glucose initially administered since the total disappearance of glucose is equal to the total amount of glycolysis+the total amount of newly synthesized glycogen (FIGS. 2 and 3). The following equation can be used to calculate newly synthesized glycogen:

Total glucose−glycolysis=newly synthesized glycogen

Determining newly synthesized glycogen is useful because it is widely believed to be an early marker for an elevated risk of insulin resistance, diabetes and cardiovascular disease. That is, the more glycogen formed from a given amount of glucose administered (as opposed to more glycolysis and less glycogen formed) the higher the risk for developing insulin resistance, diabetes and cardiovascular disease. Glycogen formation is also an early marker for an elevated risk of cerebrovascular disease.

In another variation, the rate of appearance of glycogen ($Ra_{glycogen}$), i.e., the rate of glycogen synthesis, may be determined by subtracting the rate of appearance of glycolysis ($Ra_{glycolysis}$) from the rate of disappearance of glucose ($Rd_{glucose}$). The following equation can be used to calculate the rate of new glycogen synthesis:

$Rd_{glucose} - Ra_{glycolysis} = Ra_{glycogen}$

Knowing the rate of appearance of glycogen (i.e., the rate of glycogen synthesis) provides additional useful information as a slower rate of glycogen synthesis may be associated with an elevated risk of developing diabetes, cardiovascular disease, and cerebrovascular disease. Furthermore, a slower rate of glycogen synthesis together with an increase in newly synthesized glycogen may be associated with an elevated risk of developing diabetes, cardiovascular disease, and cerebrovascular disease.

Similarly, knowing glycolysis may also be useful for determining an elevated risk of diabetes, cardiovascular disease, and cerebrovascular disease. Knowing the rate of glycolysis provides additional information useful for determining an elevated risk, as described above for the rate of glycogen synthesis. Glycolysis and the rate of glycolysis may be determined by measuring the amount of $^2H_2O$ formed after administration of H-Glucose, as is described supra.

In another variation, the one or more chemical compositions may be glycogen. Glycogen may be measured directly by direct sampling using invasive or non-invasive procedures well known in the art. In a further variation, the one or more chemical compositions may be triglycerides. In a further variation, the method may be used to determine new triglyceride synthesis.

In another variation, the one or more chemical compositions may be compounds that include triglyceride-fatty acids. In a further variation, the method may be used to calculate new fatty acid synthesis.

In a still further variation, the method may be used to calculate the ratio of labeled fatty acids to stored fatty acids. In a still further variation, the method may be used to calculate the proportion of administered fatty acids undergoing fatty acid oxidation.

In another variation, the chemical composition may include a protein.

In a further variation, the composition may include DNA. The measurement of DNA incorporation may then be used to determine the rate of new cell proliferation.

The one or more chemical compositions may also be purified, partially purified, or optionally, isolated, by conventional purification methods including high performance liquid chromatography (HPLC), fast performance liquid chromatography (FPLC), gas chromatography, gel electrophoresis, and/or any other separation methods.

The one or more chemical compositions may be hydrolyzed or otherwise degraded to form smaller subunits. Hydrolysis or other degradation methods include any method known in the art, including, but not limited to, chemical hydrolysis (such as acid hydrolysis) and biochemical hydrolysis (such as enzyme cleavage or degradation). Hydrolysis or degradation may be conducted either before or after purifying and/or isolating the one or more chemical compositions. For example, polymers formed of monosaccharides may be degraded to form smaller units of multiple monosaccharide residues, and/or optionally, monosaccharide constituents. Glycogen may be degraded chemically or proteolytically to form polysaccharides formed from glucose residues, or optionally, glucose monomers. Proteins may be chemically or proteolytically degraded to form oligopeptides, or optionally, amino acids. Fatty acids may be degraded to form ketone bodies, carbon dioxide, and water. DNA may be degraded to form polynucleotides, oligonucleotides, nucleotides, nucleosides, nucleic acid bases, or nucleic acid backbones. Degradation products may be partially purified, or optionally, isolated, by conventional purification methods including high performance liquid chromatography (HPLC), fast performance liquid chromatography (FPLC), gas chromatography, gel electrophoresis, and/or any other methods known in the art.

v) Calculating Kinetic Parameters

Rates or total amounts of $^2$H incorporation into water may be calculated. Rates of incorporation into other biopolymers may also be calculated. In one variation, the rate of incorporation of $^2$H into water may be calculated. In another variation, the rate of degradation of compounds containing labeled sugars or fatty acids may be measured. In a further variation, the biosynthesis and degradation rates of biopolymers such as glucose, glycogen, glycerol-triglyceride, triglyceride fatty acid, proteins, and DNA may also be determined. In still another variation, both rates of labeled water formation and biopolymer formation may be calculated. Finally, the rates may be used individually, or in combination, to diagnose, prognose, or identify the risk of metabolic or metabolically-related diseases or disorders.

Synthesis and degradation rates may be calculated by mass isotopomer distribution analysis (MIDA), which may be used to calculate the degradation or biosynthesis rates of metabolites and/or water by measuring the production of labeled water. In addition, MIDA may be used to calculate the synthesis rate of biopolymers such as glucose, glycogen, glycerol-triglyceride, triglyceride fatty acid, proteins, and DNA after the sugar or fatty acid containing metabolites are metabolized.

Variations of the MIDA combinatorial algorithm are discussed in a number of different sources known to one skilled in the art. Specifically, the MIDA calculation methods are the subject of U.S. Pat. No. 5,336,686, incorporated herein by reference. The method is further discussed by Hellerstein and Neese (1999), incorporated herein by reference, as well as Patterson and Wolfe (1993), and Kelleher and Masterson (1992).

In addition to the above-cited references, calculation software implementing the method is publicly available from Marc Hellerstein at the University of California, Berkeley.

In brief, calculation of the number (n) of metabolically exchanged H-atoms between sugars or fatty acids and cellular water was by combinatorial analysis, or MIDA. The relative fraction of double-labeled to single-labeled sugars or fatty acid molecules reveals n if the precursor pool enrichment of $^2$H (p) is known. If one assumes that p reflects body labeled water enrichment, then n can be calculated by combinatorial analysis.

Fractional abundances of mass isotopomers result from mixing natural abundance molecules with molecules newly synthesized from a pool of labeled monomers characterized by the parameter p. A mixture of this type can be fully characterized by f, the fraction new, and p. The algorithm proceeds in step-wise fashion, beginning with the simplest calculation, a molecule synthesized from a single element containing isotopes with the same fractional abundances that occur in nature and not mixed with any other molecules. We then proceed to molecules containing more than one element with all isotopes at natural abundance; then to non-polymeric molecules containing different elements, some of which are in groups whose isotope composition is not restricted to natural abundance but is variable; then to polymeric molecules containing combinations of repeating chemical units (monomers), wherein the monomers are either unlabeled (containing a natural abundance distribution of isotopes) or potentially labeled (containing an isotopically-perturbed element group); and finally to mixtures of polymeric molecules, composed of both natural abundance polymers and potentially labeled polymers, the latter containing combinations of natural abundance and isotopically-perturbed units.

The last-named calculation addresses the condition generally present in a biological system, wherein polymers newly synthesized during the period of an isotope incorporation experiment are present along with pre-existing, natural abundance polymers and the investigator is interested in determining the proportion of each that is present, in order to infer synthesis rates or related parameters.

Methods of Use

Using the methods disclosed herein, metabolic consequences of nutrient ingestion may be determined for a number of metabolites in an individual. These consequences may be applied for diagnostic and/or monitoring uses. There are numerous research and clinical applications of this technique.

In one variation, the effect of a drug agent on an individual may be monitored. A change in the sugar or fatty acid metabolism in an individual to which a drug agent has been administered identifies the drug agent as capable of altering the sugar or fatty acid metabolism of the individual. The drug agent may be administered to the same individual, or different living systems. Drug agents may be any chemical compound or composition known in the art. Drug agents include, but are not limited to, any chemical compound or composition disclosed in, for example, the 13th Edition of *The Merck Index* (a U.S. publication, Whitehouse Station, N.J., USA), incorporated herein by reference in its entirety.

In another variation, drug agents can be at least partially identified as to desirable or undesirable (or both) characteristics. Such information is useful in evaluating whether a drug agent should be advanced in clinical development, for example, whether a drug agent should be tested in in vivo animal models, whether it should be the subject of clinical trials, and whether it should be advanced further in the clinical trial setting (e.g., after an IND filing and/or after completion of phase I, phase II and/or phase III trials). Once advanced through the filing and approval of an NDA, it is readily apparent that the methods of the present invention allow for the early identification of drug agents useful in the treatment of metabolic diseases such as diabetes, cardiovascular disease, and other obesity-related diseases or disorders. In another embodiment, the fate of nutrients as surrogates during FDA trials may be monitored.

In another variation, the methods may be used to identify individuals at risk for diabetes. In another variation, the methods may be used to identify patients at risk for high-fat diet-induced obesity.

In another variation, the methods may be used to diagnose, prognose, or identify the risk of insulin resistance/diabetes mellitus (type II diabetes) in an individual. In a further variation, the methods may be used to diagnose, prognose, or identify the risk of high-fat diet-induced obesity in an individual. In another variation, the methods may be used to monitor the effects of interventions or treatment methods to prevent or reverse insulin resistance/diabetes mellitus or high-fat diet-induced obesity.

Isotopically-Perturbed Molecules

In another variation, the methods provide for the production of isotopically-perturbed molecules (e.g., labeled fatty acids, lipids, carbohydrates, proteins, nucleic acids and the like). These isotopically-perturbed molecules comprise information useful in determining the flux of molecules within the metabolic pathways of interest. Once isolated from a cell and/or a tissue of an organism, one or more isotopically-perturbed molecules are analyzed to extract information as described, supra.

In other variations, the methods may be used to diagnose or treat wasting diseases or disorders, hypoglycemia, or glycogen storage disease.

Kits

In another aspect, the invention provides kits for analyzing the metabolic fate of glucose or fatty acids in vivo. The kits may include labeled glucose or fatty acids. The kits may also include chemical compounds known in the art for isolating chemical and biochemical compounds from urine, bone, or muscle and/or chemicals necessary to get a tissue sample, automated calculation software for combinatorial analysis, and instructions for use of the kit are optionally included in the kit.

Other kit components, such as tools for administration of compounds containing labeled sugars and fatty acids are optionally included. Tools may include measuring cups, needles, syringes, pipettes, IV tubing), may optionally be provided in the kit. Similarly, instruments for obtaining samples from the subject (e.g., specimen cups, needles, syringes, and tissue sampling devices) may also be optionally provided.

Information Storage Devices

The invention also provides for information storage devices such as paper reports or data storage devices comprising data collected from the methods of the present invention. An information storage device includes, but is not limited to, written reports on paper or similar tangible medium, written reports on plastic transparency sheets or microfiche, and data stored on optical or magnetic media (e.g., compact discs, digital video discs, magnetic discs, and the like), or computers storing the information whether temporarily or permanently. The data may be at least partially contained within a computer and may be in the form of an electronic mail message or attached to an electronic mail message as a separate electronic file. The data within the information storage devices may be "raw" (i.e., collected but unanalyzed), partially analyzed, or completely analyzed. Data analysis may be by way of computer or some other automated device or may be done manually. The information storage device may be used to download the data onto a separate data storage system (e.g., computer, hand-held computer, and the like) for further analysis or for display or both. Alternatively, the data within the information storage device may be printed onto paper, plastic transparency sheets, or other similar tangible medium for further analysis or for display or both. The information storage device may provide for retrieval of the data. Such retrieval can be for the purpose of display and/or for further analysis or for any other purpose.

The following examples are provided to show that the methods of the invention may be used to determine the fate of metabolic glucose or fatty acids. Those skilled in the art will recognize that while specific embodiments have been illustrated and described, they are not intended to limit the invention.

EXAMPLES

Example 1

Kinetic OGTT

Glycolytic Disposal of Glucose in Normal Rats and Mice

The kinetic oral glucose tolerance test for mice and rats is depicted in FIGS. 5 and 6, respectively. The figures depict percent glycolysis, measured by deuterium incorporation into water following administration of deuterium-labeled glucose.

Sprague-Dawley rats (200-250 g, Simonsen Inc., Gilroy Calif.) and C57Blk/6ksj mice (10-15 g, Jackson Laboratories, Bar Harbor Me.) were used. Housing was in individual cages for rats and groups of 5 for mice. Feeding was ad-libitum with Purina® rodent chow. All studies received prior approval from the UC Berkeley Animal Care and Use Committee.

The $^2$H-glucose labeling protocol consisted of an initial intraperitoneal (ip) injection of 99.9% [6,6-$^2$H$_2$]glucose. For labeling rats and mice, 2 mg labeled glucose per gram body weight were introduced. Body water was collected as serum at various timepoints.

Glycolysis was measured by measuring deuterium in body water as a percent of administered [6,6-$^2$H$_2$]glucose normalized to account for different molar quantities of deuterium in molecular glucose and molecular water. Deuterized water was measured by isotope ratio mass spectrometry.

Example 2

Kinetic OGTT

Glycolytic Disposal of Glucose in Normal Rats and Mice

A kinetic oral glucose tolerance test in a human subject is depicted in FIG. 4. The figure depicts percent glycolysis, measured by deuterium incorporation into water following ingestion of deuterium labeled glucose.

The $^2$H-glucose labeling protocol consisted of an oral ingestion of 99.9% [6,6-$^2$H$_2$]glucose. 15 grams glucose in 50 grams oral load (30% [6,6-$^2$H$_2$]) were ingested by the human subject. Body water was collected as serum at various time-points.

Glycolysis was measured by measuring deuterium in body water as a percent of administered [6,6-$^2$H$_2$]glucose normalized to account for different molar quantities of deuterium in molecular glucose and molecular water. Deuterized water was measured by isotope ratio mass spectrometry.

Example 3

[6,6-$^2$H$_2$]glucose was administered orally (15 grams in water) to a lean male human subject (Subject #1), to an overweight but not obese male human subject (Subject #2), to an obese female human subject (Subject #3), and to a lean male human subject with HIV/AIDS (Subject #4). Blood samples were collected (10 cc) every hour for four hours. $^2$H content of blood glucose was measured by isolating glucose from blood and preparing into a form compatible with isotope ratio mass spectrometry. The isotopic ($^2$H$_2$O) content of body water was measured by isolating water from the blood and preparing into a form compatible with isotope ratio mass spectrometry. Mass spectrometry was performed to calculate the fraction of H from $^2$H-glucose released into body water. This represents glycolysis/oxidation from the administered glucose load. Measurement of H-glucose content measured by mass spectrometry was compared to administered $^2$H content of administered $^2$H-glucose to calculate the body's production rate of glucose. Fasting plasma insulin levels were measured by radioimmunoassay (RIA) specific for insulin. RIA kits are readily available from a variety of commercial sources such as Linco Research Inc., St. Charles, Mo., USA or Phoenix Pharmaceutical, Inc., Belmont, Calif., USA. Plasma glucose levels were measured by the use of glucose oxidase, a technique well known in the art. Kits containing glucose oxidase for the measurement of glucose are readily available, for example from Sigma Aldrich, St. Louis, Mo., USA. Table 1 depicts the results.

TABLE 1

Subjects Undergoing $^2$H-OGTT (75 g glucose; 15 g [6,6-$^2$H] Glucose)

| Subject # | BMI (kg/m$^2$) | Gender | Fasting Plasma Insulin (μU/mL) | Peak Plasma Glucose (mg/dL) | Glycolysis (mMoles $^2$H$_2$O produced) 2 h | 4 h |
|---|---|---|---|---|---|---|
| 1 | 23.5 | M | <15 | 105 | 25 | 50 |
| 2 | 27.2 | M | 20 | 96 | 26 | 41 |
| 3 | 31.8 | F | 33 | 108 | 15 | 34 |
| 4 | 23.5 | M | >30 | 225 | 16 | 33 |

BMI = Body Mass Index
Plasma glucose >200 mg/dL during $^2$H-OGTT indicates glucose intolerance or diabetes
Plasma insulin >20 indicates hyperinsulinemia/insulin resistance
Maximal production of $^2$H$_2$O from 15 g $^2$H-glucose is 82 × 10$^{-3}$ moles As can be seen from table 1, supra, Subject #1 is a normal, lean healthy male subject (normal control). Subject #2 is a normal, overweight but not obese healthy male subject. Subject #3 is a normal, obese healthy female. Subject #4 is a lean male with HIV/AIDS. The data identifies clinically evident glucose intolerant or diabetic individuals despite the absence of obesity (Subject #4). Subject #4 is an HIV positive male with AIDS receiving protease-inhibitor containing anti-retroviral therapy. People with AIDS who receive anti-retroviral treatments often develop a glucose intolerant or diabetic phenotype. The data in table 1 also identifies pre-diabetic (insulin resistant) individuals before glucose intolerance is apparent (Subject #3). This method allows for early detection of glucose intolerance.

REFERENCES

1. Veerkamp J H, Van Moerkerk H T B, Glatz J F C, Zuurveld J G E M, Jacobs A E M, Wagenmakers A J M. $^{14}$CO$_2$ production is no adequate measure of $^{14}$C-fatty acid oxidation. Biochem Med Metab Biol 35:248-59, 1986.
2. Malewiak M I, Griglio S, Kalopissis A D, LeLiepure X. Oleate metabolism in isolated hepatocytes from lean and obese Zucker rats. Influence of a high-fat diet and in vitro response to glucagon. Metab Clin Exp 32:661-8, 1993.
3. Van Hinsbergh V, Veerkamp J H, van Moerkerk H T B. Palmitate oxidation by rat skeletal muscle mitochondria. Comparison of polarographic and radiochemical experiments Arch Biochem Biophys 190:762, 1978.
4. Hellerstein M K. Methods for measurement of fatty acid and cholesterol metabolism. In: Howard B, Packard C, eds. Current Opinion in Lipidology 6:172-81, 1995.
5. Katz, J., and R. Rognstad. Futile cycles in the metabolism of glucose. In: Current Topics in Cellular Regulation. Vol 10, edited by B. Horecker and E. Stadman. New York: Academic Press, 1976, p. 238-239.
6. Rossetti L, Lee Y T, Ruiz J, Aldridge S C, Shamoon H, Boden G. Quantitation of glycolysis and skeletal muscle glycogen synthesis in humans. Am J Physiol 265:E761-9, 1993.
7. Turner S, Neese R A, Murphy E, Antelo F, Thomas T, Hellerstein M K. Measurement of triglyceride synthesis and turnover in vivo by H$_2$O incorporation into the glycerol moiety and application of mass isotopomer distribution analysis. Am J Physiol, Submitted, 2002.
8. Neese R A, Misell L, Antelo F, Hoh R, Chu A, Strawford A, Christiansen M, Hellerstein M K. Measurement of DNA synthesis in slow turnover cells in vivo using $^2$H$_2$O labeling of the deoxyribose moiety: application to human adipocytes. Proc Natl Acad Sci USA, In Press, 2002.
9. Misell L, Thompson J, Antelo F, Chou Y-C, Nandi S, Neese R, Hellerstein M K. A new in vivo stable isotope method using $^2$H$_2$O for measuring mammary epithelial cell proliferation. FASEB J 14(4):A786, 2000.
10. Kim J, Neese R, Hellerstein M K. A new method to measure proliferation rates of colon epithelial cells. FASEB J 14(4):A718, 2000.
11. Antelo F, Strawford A, Neese R A, Christiansen M, Hellerstein M. Adipose triglyceride (TG) turnover and de novo lipogenesis (DNC) in humans: measurement by long-term $^2$H$_2$O labeling and mass isotopomer distribution analysis (MIDA). FASEB J 16:A400, 2002.
12. Chu A, Cesar D, Ordonez E, Hellerstein M. An in vivo method for measuring vascular smooth muscle cell (VSMC) proliferation using $^2$H$_2$O. Circulation, 2000.
13. Hellerstein M K, Neese R A, Kim Y-K, Schade-Serin V, Collins M. Measurement of synthesis rates of slow-turnover proteins from $^2$H$_2$O incorporation into non-essential amino acids (NEAA) and application of mass isotopomer distribution analysis (MIDA). FASEB J 16:A256, 2002.
14. Kim Y-K, Neese R A, Schade-Serin V, Collins M, Misell L, Hellerstein M K. Measurement of synthesis rates of slow-turnover proteins based on $^2$H$_2$O incorporation into non-essential amino acids and application of mass isotopomer distribution analysis. Biochemical J, Submitted, 2002.

15. Reaven G M. Banting lecture 1988. Role of insulin resistance in human disease. Diabetes 37(12):1595-607, 1988.

All publications, patents, and patent applications cited herein are hereby incorporated by reference in their entirety for all purposes to the same extent as if each individual publication, patent, or patent application were specifically and individually indicated to be so incorporated by reference. Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit and scope of the claims.

Applicants have not abandoned or dedicated to the public any unclaimed subject matter.

What is claimed:

1. A method of identifying the effect of a drug agent on a rate of in vivo metabolism of one or more sugars or fatty acids in an individual, the method comprising:
   (a) administering a drug agent to the individual;
   (b) administering a known quantity of $^2$H-labeled sugars or $^2$H-labeled fatty acids to an individual for a sufficient time for the $^2$H-labeled sugars or $^2$H-labeled fatty acids to be metabolized in the individual to produce $^2$H-labeled water;
   (c) obtaining one or more bodily tissues or fluids at one or more times from the individual, wherein the one or more bodily tissues or fluids comprise a portion of the $^2$H-labeled water;
   (d) determining a quantity of $^2$H present in the portion of the $^2$H-labeled water to quantify an amount of $^2$H released into body water; and
   (e) calculating a ratio of the amount of $^2$H released into body water to the known quantity of $^2$H administered as $^2$H-labeled sugars or $^2$H-labeled fatty acids to determine the rate of in vivo metabolism of the one or more of sugars or fatty acids in the individual to whom the drug agent has been administered; and
   (f) comparing the rate of in vivo metabolism of the one or more sugars or fatty acids in the individual to whom the drug agent has been administered to the rate of in vivo metabolism of the one or more sugars or fatty acids in an individual to whom the drug has not been administered to identify the effect of the drug agent on the rate of in vivo metabolism of one or more sugars or fatty acids in an individual.

2. The method of claim 1, wherein the individual to whom the drug has not been administered is the same individual to whom the drug agent has been administered at a point in time prior to administration of the drug or at a point in time after the administration of the drug sufficient for the drug to clear from the system of the individual.

3. The method according to claim 1, wherein the known quantity of $^2$H-labeled sugars comprise $^2$H-labeled glucose.

4. The method according to claim 3, wherein the $^2$H-labeled glucose is selected from the group consisting of [6,6-$^2$H$_2$]glucose, [1-$^2$H$_1$]glucose, and [1,2,3,4,5,6-$^2$H$_7$]glucose.

5. The method according to claim 1, wherein the known quantity of $^2$H-labeled sugars or $^2$H-labeled fatty acids is administered by a technique selected from the group consisting of oral, gavage, intraperitoneal, intravascular, and subcutaneous administration.

6. The method according to claim 1, wherein the individual is a mammal is selected from the group consisting of human, rodent, primate, dog, and pig.

7. The method according to claim 6, wherein the mammal is a human.

8. The method according to claim 1, wherein the one or more bodily tissues or fluids are selected from the group consisting of blood, urine, saliva, and tears.

9. The method of claim 1, wherein the one or more bodily tissues or fluids are selected from the group consisting of liver, muscle, adipose, intestine, brain, and pancreas.

10. The method of claim 1, comprising the additional step of partially purifying the portion of the $^2$H-labeled water from the one or more bodily tissues or fluids.

11. The method according to claim 1, comprising the additional step of calculating a proportion or storage rate of administered $^2$H-labeled fatty acids by calculating the proportion of $^2$H-labeled fatty acids not metabolized in the individual to produce $^2$H-labeled water.

12. The method according to claim 1, wherein the quantity of $^2$H present in the portion of the $^2$H-labeled water is determined by a method selected from the group consisting of gas chromatography/mass spectrometry, liquid chromatography-mass spectrometry, gas chromatography-pyrolysis-isotope ratio/mass spectrometry, gas chromatography-combustion-isotope ratio/mass spectrometry, cycloidal mass spectrometry, Fourier-transform-isotope ratio (IR)-spectroscopy, near IR laser spectroscopy, and isotope ratio mass spectrometry.

13. The method according to claim 1, wherein the determining step is accomplished by determining one part $^2$H in $10^7$ parts water.

14. The method according to claim 1, wherein the method further comprises identifying individuals at risk for insulin resistance and diabetes mellitus.

15. The method according to claim 1, wherein the method further comprises diagnosing high-fat diet-induced obesity.

16. The method according to claim 1, wherein the method further comprises identifying individuals at risk for high-fat diet-induced obesity.

17. The method according to claim 1, wherein the method further comprises a step of monitoring the effects of interventions to prevent or reverse insulin resistance, diabetes mellitus, and high-fat diet-induced obesity.

18. The method according to claim 1, further comprising a step of diagnosing or treating a condition selected from the group consisting of wasting disorders, hypoglycemia, and glycogen storage disease.

19. The method according to claim 1, comprising the additional step of calculating a proportion or storage rate of administered $^2$H-labeled sugars by calculating the proportion of $^2$H-labeled sugars not metabolized in the individual to produce $^2$H-labeled water.

* * * * *